US012741035B2

(12) United States Patent
Lonard et al.

(10) Patent No.: US 12,741,035 B2
(45) Date of Patent: Sep. 22, 2026

(54) UTILIZATION OF GENE TARGETING ANTIBODY FUSION PROTEINS TO PERFORM IN VIVO THERAPEUTIC GENE EDITING

(71) Applicant: Baylor College of Medicine, Houston, TX (US)

(72) Inventors: David M. Lonard, Houston, TX (US); Bert W. O'Malley, Houston, TX (US); Clifford Dacso, Houston, TX (US); Sang Jun Han, Houston, TX (US); Rohit Kumar Srivastava, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 19/094,456

(22) Filed: Mar. 28, 2025

(65) Prior Publication Data

US 2025/0269060 A1 Aug. 28, 2025

Related U.S. Application Data

(63) Continuation of application No. PCT/US2023/075304, filed on Sep. 28, 2023.

(60) Provisional application No. 63/377,616, filed on Sep. 29, 2022, provisional application No. 63/377,618, filed on Sep. 29, 2022.

(51) Int. Cl.

| | |
|---|---|
| ***A61K 48/00*** | (2006.01) |
| ***C07K 16/28*** | (2006.01) |
| ***C12N 9/22*** | (2006.01) |
| ***C12N 9/50*** | (2006.01) |
| ***C12N 15/11*** | (2006.01) |
| *A61K 38/00* | (2006.01) |

(52) U.S. Cl.

CPC ........ *A61K 48/005* (2013.01); *A61K 48/0075* (2013.01); *C07K 16/2866* (2013.01); *C12N 9/226* (2025.05); *C12N 9/506* (2013.01); *C12N 15/111* (2013.01); *A61K 38/00* (2013.01); *C07K 2317/622* (2013.01); *C07K 2319/10* (2013.01); *C07K 2319/43* (2013.01); *C12N 2310/20* (2017.05)

(58) Field of Classification Search

CPC .............. A61K 48/005; C07K 16/2866; C07K 2319/00; C12N 9/226; C12N 15/111; C12N 2310/20

See application file for complete search history.

(56) References Cited

U.S. PATENT DOCUMENTS

2022/0259616 A1 * 8/2022 Chen ...................... A61K 40/32

FOREIGN PATENT DOCUMENTS

WO 2020198151 A1 10/2020
WO 2022115611 A1 6/2022

OTHER PUBLICATIONS

Song et al. (Cancer Lett. Feb. 1, 2019:442:310-319; Epub Nov. 10, 2018). (Year: 2019).*

International Search Report dated Feb. 21, 2024, issued during examination of International Application No. PCT/US2023/075304.

* cited by examiner

*Primary Examiner* — J. E. Angell

(74) *Attorney, Agent, or Firm* — Norton Rose Fulbright US LLP

(57) ABSTRACT

Embodiments of the present disclosure concerns methods and compositions related to treatment using a CRISPR/Cas9/targeting antibody/gene targeting small guide RNA (sgRNA) fusion protein/ribonucleotide complex. The targeting of a polynucleotide of interest, such as a gene, may be effective to eradicate tumors in mammals. In some cases, sgRNA ribonucleotides with sequences designed to target any gene or genomic region are contemplated. In some embodiments, the targeting of SRC-3 in T regulatory cells in particular is effective to eradicate tumors in mammals. In specific cases, the T regulatory cells are subjected to CRISPR-based gene modification in vivo obviating the need for adoptive cell therapy. In some cases, substitutions of the CD25 targeting antibody is replaced with another antibody to recognize other cell surface antigens. In some cases, sgRNA ribonucleotides with sequences designed to target any gene or genomic region are described.

18 Claims, 3 Drawing Sheets

Specification includes a Sequence Listing.

FIG. 1
Stop
Linker
Linker
Linker
Linker
6His

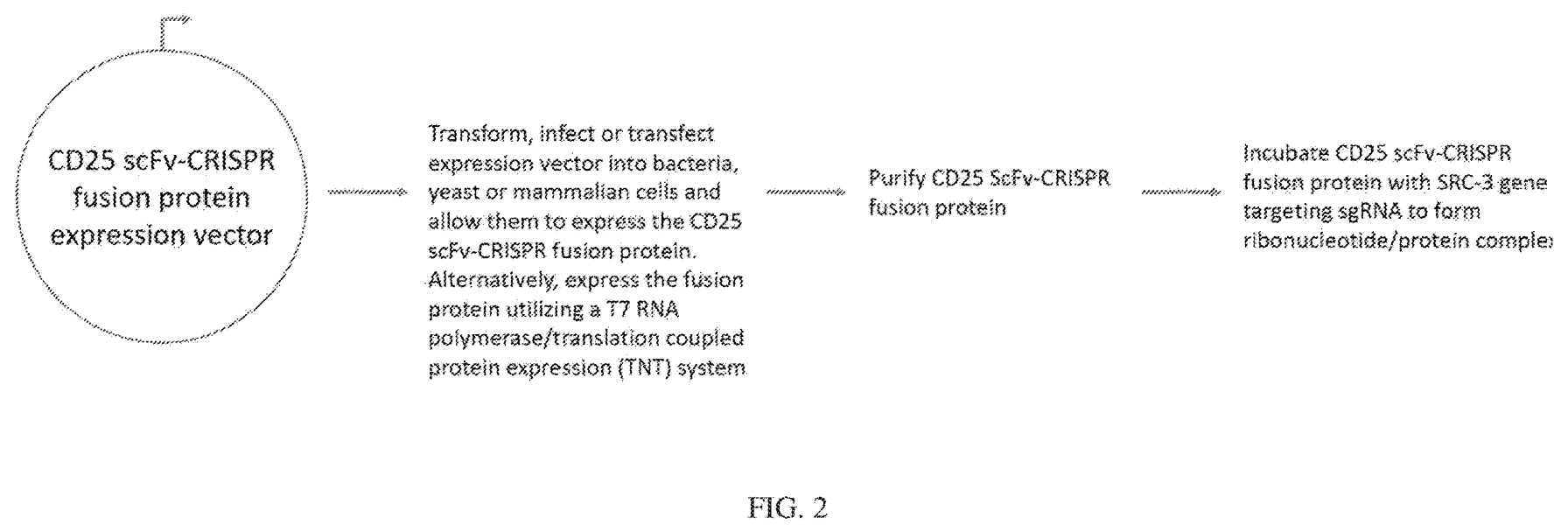

CD25 scFv-CRISPR fusion protein expression vector

Transform, infect or transfect expression vector into bacteria, yeast or mammalian cells and allow them to express the CD25 scFv-CRISPR fusion protein. Alternatively, express the fusion protein utilizing a T7 RNA polymerase/translation coupled protein expression (TNT) system Purify CD25 ScFv-CRISPR fusion protein Incubate CD25 scFv-CRISPR fusion protein with SRC-3 gene targeting sgRNA to form ribonucleotide/protein comple

FIG. 2

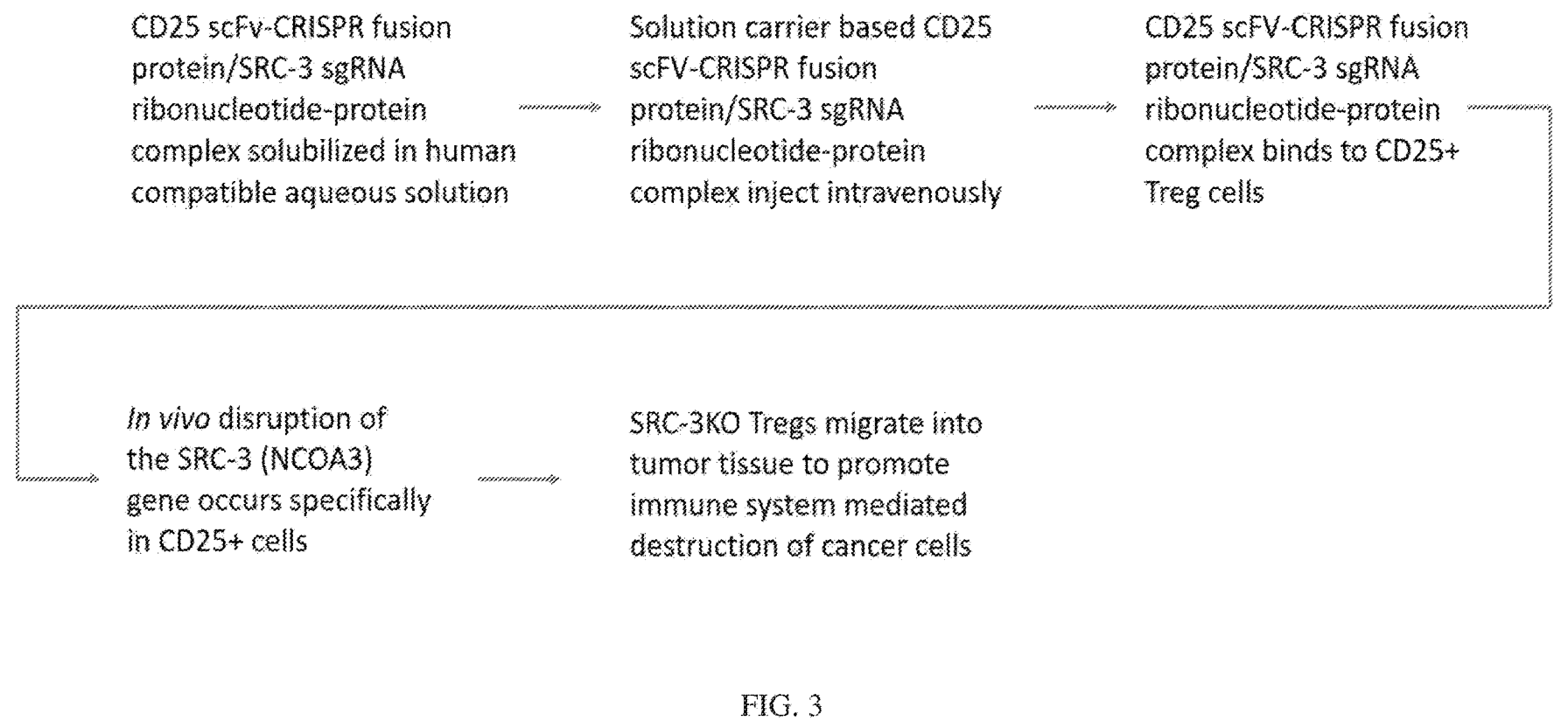

CD25 scFv-CRISPR fusion protein/SRC-3 sgRNA ribonucleotide-protein complex solubilized in human compatible aqueous solution Solution carrier based CD25 scFV-CRISPR fusion protein/SRC-3 sgRNA ribonucleotide-protein complex inject intravenously CD25 scFV-CRISPR fusion protein/SRC-3 sgRNA ribonucleotide-protein complex binds to CD25+ Treg cells

*In vivo* disruption of the SRC-3 (NCOA3) gene occurs specifically in CD25+ cells SRC-3KO Tregs migrate into tumor tissue to promote immune system mediated destruction of cancer cells

FIG. 3

SEQUENCE LISTING

```
Sequence total quantity: 24
SEQ ID NO: 1            moltype = AA  length = 6
FEATURE                 Location/Qualifiers
source                  1..6
                        mol_type = protein
                        organism = synthetic construct
SEQUENCE: 1
HHHHHH                                                              6

SEQ ID NO: 2            moltype = AA  length = 16
FEATURE                 Location/Qualifiers
source                  1..16
                        mol_type = protein
                        organism = synthetic construct
SEQUENCE: 2
KLALKLALKA LKAALK                                                   16

SEQ ID NO: 3            moltype =   length =
SEQUENCE: 3
000

SEQ ID NO: 4            moltype = AA  length = 5
FEATURE                 Location/Qualifiers
source                  1..5
                        mol_type = protein
                        organism = synthetic construct
SEQUENCE: 4
LFPTI                                                               5

SEQ ID NO: 5            moltype = AA  length = 1367
FEATURE                 Location/Qualifiers
source                  1..1367
                        mol_type = protein
                        organism = synthetic construct
SEQUENCE: 5
DKKYSIGLDI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
```

```
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 6           moltype =   length =
SEQUENCE: 6
000

SEQ ID NO: 7           moltype = AA  length = 7
FEATURE                Location/Qualifiers
source                 1..7
                       mol_type = protein
                       organism = synthetic construct
SEQUENCE: 7
ENLYFQG                                                            7

SEQ ID NO: 8           moltype =   length =
SEQUENCE: 8
000

SEQ ID NO: 9           moltype = AA  length = 9
FEATURE                Location/Qualifiers
source                 1..9
                       mol_type = protein
                       organism = synthetic construct
SEQUENCE: 9
DYKDDDDKG                                                          9

SEQ ID NO: 10          moltype = AA  length = 239
FEATURE                Location/Qualifiers
source                 1..239
                       mol_type = protein
                       organism = synthetic construct
SEQUENCE: 10
QVQLVQSGAE VKKPGSSVKV SCKASGYTFT SYRMHWVRQA PGQGLEWIGY INPSTGYTEY  60
NQKFKDKATI TADESTNTAY MELSSLRSED TAVYYCARGG GVFDYWGQGT LVTVSSGGGG  120
SGGGGSGGGG SDIQMTQSPS TLSASVGDRV ITITCSASSS ISYMHWYQQK PGKAPKLLIY  180
TTSNLASGVP ARFSGSGSGT EFTLTISSLQ PDDFATYYCH QRSTYPLTFG QGTKVEVKR   239

SEQ ID NO: 11          moltype = AA  length = 1367
FEATURE                Location/Qualifiers
source                 1..1367
                       mol_type = protein
                       organism = synthetic construct
SEQUENCE: 11
DKKYSIGLDI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 12          moltype = DNA  length = 18
FEATURE                Location/Qualifiers
source                 1..18
                       mol_type = other DNA
                       organism = synthetic construct
SEQUENCE: 12
caccaccatc atcatcat                                                18
```

```
SEQ ID NO: 13          moltype = DNA  length = 48
FEATURE                Location/Qualifiers
source                 1..48
                       mol_type = other DNA
                       organism = synthetic construct
SEQUENCE: 13
aagctggccc tgaagctggc cctgaaggcc ctgaaggccg ccctgaag              48

SEQ ID NO: 14          moltype =   length =
SEQUENCE: 14
000

SEQ ID NO: 15          moltype = DNA  length = 15
FEATURE                Location/Qualifiers
source                 1..15
                       mol_type = other DNA
                       organism = synthetic construct
SEQUENCE: 15
ctgttcccca ccatc                                                  15

SEQ ID NO: 16          moltype = DNA  length = 4101
FEATURE                Location/Qualifiers
source                 1..4101
                       mol_type = other DNA
                       organism = synthetic construct
SEQUENCE: 16
gacaagaagt acagcatcgg cctggacatc ggcaccaaca gcgtgggctg ggccgtgatc  60
accgacgagt acaaggtgcc cagcaagaag ttcaaggtgc tgggcaacac cgacaggcac  120
agcatcaaga agaacctgat cggcgccctg ctgttcgaca gcggcgagac cgccgaggcc  180
accaggctga agaggaccgc caggaggagg tacaccagga ggaagaacag gatctgctac  240
ctgcaggaga tcttcagcaa cgagatggcc aaggtggacg acagcttctt ccacaggctg  300
gaggagagct tcctggtgga ggaggacaag aagcacgaga ggcaccccat cttcggcaac  360
atcgtggacg aggtggccta ccacgagaag taccccacca tctaccacct gaggaagaag  420
ctggtggaca gcaccgacaa ggccgacctg aggctgatct acctggccct ggcccacatg  480
atcaagttca ggggccactt cctgatcgag ggcgacctga accccgacaa cagcgacgtg  540
gacaagctgt tcatccagct ggtgcagacc tacaaccagc tgttcgagga gaaccccatc  600
aacgccagcg gcgtggacgc caaggccatc ctgagcgcca ggctgagcaa gagcaggagg  660
ctggagaacc tgatcgccca gctgcccggc gagaagaaga acggcctgtt cggcaacctg  720
atcgccctga gcctgggcct gacccccaac ttcaagagca acttcgacct ggccgaggac  780
gccaagctgc agctgagcaa ggacacctac gacgacgacc tggacaacct gctggcccag  840
atcggcgacc agtacgccga cctgttcctg gccgccaaga acctgagcga cgccatcctg  900
ctgagcgaca tcctgagggt gaacaccgag atcaccaagg ccccctgag cgccagcatg  960
atcaagaggt acgacgagca ccaccaggac ctgaccctgc tgaaggccct ggtgaggcag  1020
cagctgcccg agaagtacaa ggagatcttc ttcgaccaga gcaagaacgg ctacgccggc  1080
tacatcgacg gcggcgccag ccaggaggag ttctacaagt tcatcaagcc catcctggag  1140
aagatggacg gcaccgagga gctgctggtg aagctgaaca gggaggacct gctgaggaag  1200
cagaggacct tcgacaacgg cagcatcccc caccagatcc acctgggcga gctgcacgcc  1260
atcctgagga ggcaggagga cttctacccc ttcctgaagg acaacaggga gaagatcgag  1320
aagatcctga ccttcaggat ccccctactac gtgggccccc tggccagggg caacagcagg  1380
ttcgcctgga tgaccaggaa gagcgaggag accatcaccc cctggaactt cgaggaggtg  1440
gtggacaagg gcgccagcgc ccagagcttc atcgagagga tgaccaactt cgacaagaac  1500
ctgcccaacg agaaggtgct gcccaagcac agcctgctgt acgagtactt caccgtgtac  1560
aacgagctga ccaaggtgaa gtacgtgacc gagggcatga ggaagcccgc cttcctgagc  1620
ggcgagcaga agaaggccat cgtggacctg ctgttcaaga ccaacaggaa ggtgaccgtg  1680
aagcagctga aggaggacta cttcaagaag atcgagtgct tcgacagcgt ggagatcagc  1740
ggcgtggagg acaggttcaa cgccagcctg ggcacctacc acgacctgct gaagatcatc  1800
aaggacaagg acttcctgga caacgaggag aacgaggaca tcctggagga catcgtgctg  1860
accctgaccc tgttcgagga cagggagatg atcgaggaga ggctgaagac ctacgcccac  1920
ctgttcgacg acaaggtgat gaagcagctg aagaggagga ggtacaccgg ctggggcagg  1980
ctgagcagga agctgatcaa cggcatcagg gacaagcaga gcggcaagac catcctggac  2040
ttcctgaaga gcgacggctt cgccaacagg aacttcatgc agctgatcca cgacgacagc  2100
ctgaccttca aggaggacat ccagaaggcc caggtgagcg gccagggcga cagcctgcac  2160
gagcacatcg ccaacctggc cggcagcccc gccatcaaga agggcatcct gcagaccgtg  2220
aaggtggtgg acgagctggt gaaggtgatg ggcaggcaca agcccgagaa catcgtgatc  2280
gagatggcca gggagaacca gaccacccag aagggccaga agaacagcag ggagaggatg  2340
aagaggatcg aggagggcat caaggagctg ggcagccaga tcctgaagga gcaccccgtg  2400
gagaacaccc agctgcagaa cgagaagctg tacctgtact acctgcagaa cggcagggac  2460
atgtacgtgg accaggagct ggacatcaac aggctgagcg actacgacgt ggaccacatc  2520
gtgccccaga gcttcctgaa ggacgacagc atcgacaaca aggtgctgac caggagcgac  2580
aagaacaggg gcaagagcga caacgtgccc agcgaggagg tggtgaagaa gatgaagaac  2640
tactggaggc agctgctgaa cgccaagctg atcacccaga ggaagttcga caacctgacc  2700
aaggccgaga ggggcggcct gagcgagctg gacaaggccg gcttcatcaa gaggcagctg  2760
gtggagacca ggcagatcac caagcacgtg gcccagatcc tggacagcag gatgaacacc  2820
aagtacgacg agaacgacaa gctgatcagg gaggtgaagg tgatcaccct gaagagcaag  2880
ctggtgagcg acttcaggaa ggacttccag ttctacaagg tgagggagat caacaactac  2940
caccacgccc acgacgccta cctgaacgcc gtggtgggca ccgccctgat caagaagtac  3000
cccaagctgg agagcgagtt cgtgtacggc gactacaagg tgtacgacgt gaggaagatg  3060
atcgccaaga gcgagcagga gatcggcaag gccaccgcca agtacttctt ctacagcaac  3120
atcatgaact tcttcaagac cgagatcacc ctggccaacg gcgagatcag gaagaggccc  3180
```

```
ctgatcgaga ccaacggcga gaccggcgag atcgtgtggg acaagggcag ggacttcgcc  3240
accgtgagga aggtgctgag catgccccag gtgaacatcg tgaagaagac cgaggtgcag  3300
accggcggct tcagcaagga gagcatcctg cccaagagga acagcgacaa gctgatcgcc  3360
aggaagaagg actgggaccc caagaagtac ggcggcttcg acagccccac cgtggcctac  3420
agcgtgctgg tggtggccaa ggtggagaag ggcaagagca agaagctgaa gagcgtgaag  3480
gagctgctgg gcatcaccat catggagagg agcagcttcg agaagaaccc catcgacttc  3540
ctggaggcca agggctacaa ggaggtgaag aaggacctga tcatcaagct gcccaagtac  3600
agcctgttcg agctggagaa cggcaggaag aggatgctgg ccagcgccgg cgagctgcag  3660
aagggcaacg agctggccct gcccagcaag tacgtgaact tcctgtacct ggccagccac  3720
tacgagaagc tgaagggcag ccccgaggac aacgagcaga agcagctgtt cgtggagcag  3780
cacaagcact acctggacga gatcatcgag cagatcagcg agttcagcaa gagggtgatc  3840
ctggccgacg ccaacctgga caaggtgctg agcgcctaca acaagcacag ggacaagccc  3900
atcagggagc aggccgagaa catcatccac ctgttcaccc tgaccaacct gggcgccccc  3960
gccgccttca agtacttcga caccaccatc gacaggaaga ggtacaccag caccaaggag  4020
gtgctggacg ccaccctgat ccaccagagc atcaccggcc tgtacgagac caggatcgac  4080
ctgagccagc tgggcggcga c                                            4101

SEQ ID NO: 17          moltype =   length =
SEQUENCE: 17
000

SEQ ID NO: 18          moltype = DNA  length = 21
FEATURE                Location/Qualifiers
source                 1..21
                       mol_type = other DNA
                       organism = synthetic construct
SEQUENCE: 18
gagaacctgt acttccaggg c                                            21

SEQ ID NO: 19          moltype =   length =
SEQUENCE: 19
000

SEQ ID NO: 20          moltype = DNA  length = 30
FEATURE                Location/Qualifiers
source                 1..30
                       mol_type = other DNA
                       organism = synthetic construct
SEQUENCE: 20
gactacaagg acgacgacga caagggctga                                   30

SEQ ID NO: 21          moltype = DNA  length = 717
FEATURE                Location/Qualifiers
source                 1..717
                       mol_type = other DNA
                       organism = synthetic construct
SEQUENCE: 21
caggtgcagc tggtgcagag cggcgccgag gtgaagaagc ccggcagcag cgtgaaggtg  60
agctgcaagg ccagcggcta caccttcacc agctacagga tgcactgggt gaggcaggcc  120
cccggccagg gcctggagtg gatcggctac atcaacccca gcaccggcta caccgagtac  180
aaccagaagt tcaaggacaa ggccaccatc accgccgacg agagcaccaa caccgcctac  240
atggagctga gcagcctgag gagcgaggac accgccgtgt actactgcgc caggggcggc  300
ggcgtgttcg actactgggg ccagggcacc ctggtgaccg tgagcagcgg cggcggcggc  360
agcggcggcg gcggcagcgg cggcggcggc agcgacatcc agatgaccca gagccccagc  420
accctgagcg ccagcgtggg cgacagggtg atcaccatca cctgcagcgc cagcagcagc  480
atcagctaca tgcactggta ccagcagaag cccggcaagg cccccaagct gctgatctac  540
accaccagca acctggccag cggcgtgccc gccaggttca gcggcagcgg cagcggcacc  600
gagttcaccc tgaccatcag cagcctgcag cccgacgact tcgccaccta ctactgccac  660
cagaggagca cctaccccct gaccttcggc cagggcacca aggtggaggt gaagagg     717

SEQ ID NO: 22          moltype = DNA  length = 4101
FEATURE                Location/Qualifiers
source                 1..4101
                       mol_type = other DNA
                       organism = synthetic construct
SEQUENCE: 22
gacaagaagt acagcatcgg cctggacatc ggcaccaaca gcgtgggctg ggccgtgatc  60
accgacgagt acaaggtgcc cagcaagaag ttcaaggtgc tgggcaacac cgacaggcac  120
agcatcaaga agaacctgat cggcgccctg ctgttcgaca gcggcgagac cgccgaggcc  180
accaggctga agaggaccgc caggaggagg tacaccagga ggaagaacag gatctgctac  240
ctgcaggaga tcttcagcaa cgagatggcc aaggtggacg acagcttctt ccacaggctg  300
gaggagagct tcctggtgga ggaggacaag aagcacgaga ggcaccccat cttcggcaac  360
atcgtggacg aggtggccta ccacgagaag taccccacca tctaccacct gaggaagaag  420
ctggtggaca gcaccgacaa ggccgacctg aggctgatct acctggccct ggcccacatg  480
atcaagttca ggggccactt cctgatcgag ggcgacctga accccgacaa cagcgacgtg  540
gacaagctgt tcatccagct ggtgcagacc tacaaccagc tgttcgagga gaaccccatc  600
aacgccagcg gcgtggacgc caaggccatc ctgagcgcca ggctgagcaa gagcaggagg  660
ctggagaacc tgatcgccca gctgcccggc gagaagaaga acggcctgtt cggcaacctg  720
atcgccctga gcctgggcct gacccccaac ttcaagagca acttcgacct ggccgaggac  780
```

```
gccaagctgc agctgagcaa ggacacctac gacgacgacc tggacaacct gctggcccag  840
atcggcgacc agtacgccga cctgttcctg gccgccaaga acctgagcga cgccatcctg  900
ctgagcgaca tcctgagggt gaacaccgag atcaccaagg ccccccctgag cgccagcatg  960
atcaagaggt acgacgagca ccaccaggac ctgaccctgc tgaaggccct ggtgaggcag  1020
cagctgcccg agaagtacaa ggagatcttc ttcgaccaga gcaagaacgg ctacgccggc  1080
tacatcgacg gcggcgccag ccaggaggag ttctacaagt tcatcaagcc catcctggag  1140
aagatggacg gcaccgagga gctgctggtg aagctgaaca gggaggacct gctgaggaag  1200
cagaggacct tcgacaacgg cagcatcccc caccagatcc acctgggcga gctgcacgcc  1260
atcctgagga ggcaggagga cttctacccc ttcctgaagg acaacaggga gaagatcgag  1320
aagatcctga ccttcaggat cccctactac gtgggccccc tggccagggg caacagcagg  1380
ttcgcctgga tgaccaggaa gagcgaggag accatcaccc cctggaactt cgaggaggtg  1440
gtggacaagg gcgccagcgc ccagagcttc atcgagagga tgaccaactt cgacaagaac  1500
ctgcccaacg agaaggtgct gcccaagcac agcctgctgt acgagtactt caccgtgtac  1560
aacgagctga ccaaggtgaa gtacgtgacc gagggcatga ggaagcccgc cttcctgagc  1620
ggcgagcaga agaaggccat cgtggacctg ctgttcaaga ccaacaggaa ggtgaccgtg  1680
aagcagctga aggaggacta cttcaagaag atcgagtgct tcgacagcgt ggagatcagc  1740
ggcgtggagg acaggttcaa cgccagcctg ggcacctacc acgacctgct gaagatcatc  1800
aaggacaagg acttcctgga caacgaggag aacgaggaca tcctggagga catcgtgctg  1860
accctgaccc tgttcgagga cagggagatg atcgaggaga ggctgaagac ctacgcccac  1920
ctgttcgacg acaaggtgat gaagcagctg aagaggagga ggtacaccgg ctggggcagg  1980
ctgagcagga agctgatcaa cggcatcagg gacaagcaga gcggcaagac catcctggac  2040
ttcctgaaga gcgacggctt cgccaacagg aacttcatgc agctgatcca cgacgacagc  2100
ctgaccttca aggaggacat ccagaaggcc caggtgagcg gccagggcga cagcctgcac  2160
gagcacatcg ccaacctggc cggcagcccc gccatcaaga agggcatcct gcagaccgtg  2220
aaggtggtgg acgagctggt gaaggtgatg ggcaggcaca agcccgagaa catcgtgatc  2280
gagatggcca gggagaacca gaccacccag aagggccaga agaacagcag ggagaggatg  2340
aagaggatcg aggagggcat caaggagctg ggcagccaga tcctgaagga gcaccccgtg  2400
gagaacaccc agctgcagaa cgagaagctg tacctgtact acctgcagaa cggcagggac  2460
atgtacgtgg accaggagct ggacatcaac aggctgagcg actacgacgt ggaccacatc  2520
gtgccccaga gcttcctgaa ggacgacagc atcgacaaca aggtgctgac caggagcgac  2580
aagaacaggg gcaagagcga caacgtgccc agcgaggagg tggtgaagaa gatgaagaac  2640
tactggaggc agctgctgaa cgccaagctg atcacccaga ggaagttcga caacctgacc  2700
aaggccgaga ggggcggcct gagcgagctg gacaaggccg gcttcatcaa gaggcagctg  2760
gtggagacca ggcagatcac caagcacgtg gcccagatcc tggacagcag gatgaacacc  2820
aagtacgacg agaacgacaa gctgatcagg gaggtgaagg tgatcaccct gaagagcaag  2880
ctggtgagcg acttcaggaa ggacttccag ttctacaagg tgagggagat caacaactac  2940
caccacgccc acgacgccta cctgaacgcc gtggtgggca ccgccctgat caagaagtac  3000
cccaagctgg agagcgagtt cgtgtacggc gactacaagg tgtacgacgt gaggaagatg  3060
atcgccaaga gcgagcagga gatcggcaag gccaccgcca agtacttctt ctacagcaac  3120
atcatgaact tcttcaagac cgagatcacc ctggccaacg gcgagatcag gaagaggccc  3180
ctgatcgaga ccaacggcga gaccggcgag atcgtgtggg acaagggcag ggacttcgcc  3240
accgtgagga aggtgctgag catgccccag gtgaacatcg tgaagaagac cgaggtgcag  3300
accggcggct tcagcaagga gagcatcctg cccaagagga acagcgacaa gctgatcgcc  3360
aggaagaagg actgggaccc caagaagtac ggcggcttcg acagccccac cgtggcctac  3420
agcgtgctgg tggtggccaa ggtggagaag ggcaagagca agaagctgaa gagcgtgaag  3480
gagctgctgg gcatcaccat catggagagg agcagcttcg agaagaaccc catcgacttc  3540
ctggaggcca agggctacaa ggaggtgaag aaggacctga tcatcaagct gcccaagtac  3600
agcctgttcg agctggagaa cggcaggaag aggatgctgg ccagcgccgg cgagctgcag  3660
aagggcaacg agctggccct gcccagcaag tacgtgaact tcctgtacct ggccagccac  3720
tacgagaagc tgaagggcag ccccgaggac aacgagcaga agcagctgtt cgtggagcag  3780
cacaagcact acctggacga gatcatcgag cagatcagcg agttcagcaa gagggtgatc  3840
ctggccgacg ccaacctgga caaggtgctg agcgcctaca acaagcacag ggacaagccc  3900
atcagggagc aggccgagaa catcatccac ctgttcaccc tgaccaacct gggcgccccc  3960
gccgccttca agtacttcga caccaccatc gacaggaaga ggtacaccag caccaaggag  4020
gtgctggacg ccaccctgat ccaccagagc atcaccggcc tgtacgagac caggatcgac  4080
ctgagccagc tgggcggcga c                                            4101

SEQ ID NO: 23           moltype = DNA  length = 4973
FEATURE                 Location/Qualifiers
source                  1..4973
                        mol_type = other DNA
                        organism = synthetic construct
modified_base           4971
                        mod_base = OTHER
                        note = Uracil
SEQUENCE: 23
atgcaccacc atcatcatca taagctggcc ctgaagctgg ccctgaaggc cctgaaggcc  60
gccctgaagg gccaggtgca gctggtgcag agcggcgccg aggtgaagaa gcccggcagc  120
agcgtgaagg tgagctgcaa ggccagcggc tacaccttca ccagctacag gatgcactgg  180
gtgaggcagg cccccggcca gggcctggag tggatcggct acatcaaccc cagcaccggc  240
tacaccgagt acaaccagaa gttcaaggac aaggccacca tcaccgccga cgagagcacc  300
aacaccgcct acatggagct gagcagcctg aggagcgagg acaccgccgt gtactactgc  360
gccaggggcg gcggcgtgtt cgactactgg ggccagggca ccctggtgac cgtgagcagc  420
ggcggcggcg gcagcggcgg cggcggcagc ggcggcggcg gcagcgacat ccagatgacc  480
cagagcccca gcaccctgag cgccagcgtg ggcgacaggg tgatcaccat cacctgcagc  540
gccagcagca gcatcagcta catgcactgg taccagcaga agcccggcaa ggcccccaag  600
ctgctgatct acaccaccag caacctggcc agcggcgtgc ccgccaggtt cagcggcagc  660
ggcagcggca ccgagttcac cctgaccatc agcagcctgc agcccgacga cttcgccacc  720
tactactgcc accagaggag cacctacccc ctgaccttcg gccagggcac caaggtggag  780
```

-continued

```
gtgaagaggc tgttccccac catcgacaag aagtacagca tcggcctgga catcggcacc  840
aacagcgtgg gctgggccgt gatcaccgac gagtacaagg tgcccagcaa gaagttcaag  900
gtgctgggca acaccgacag gcacagcatc aagaagaacc tgatcggcgc cctgctgttc  960
gacagcggcg agaccgccga ggccaccagg ctgaagagga ccgccaggag gaggtacacc  1020
aggaggaaga acaggatctg ctacctgcag gagatcttca gcaacgagat ggccaaggtg  1080
gacgacagct tcttccacag gctggaggag agcttcctgg tggaggagga caagaagcac  1140
gagaggcacc ccatcttcgg caacatcgtg gacgaggtgg cctaccacga gaagtacccc  1200
accatctacc acctgaggaa gaagctggtg gacagcaccg acaaggccga cctgaggctg  1260
atctacctgg ccctggccca catgatcaag ttcaggggcc acttcctgat cgagggcgac  1320
ctgaaccccg acaacagcga cgtggacaag ctgttcatcc agctggtgca gacctacaac  1380
cagctgttcg aggagaaccc catcaacgcc agcggcgtgg acgccaaggc catcctgagc  1440
gccaggctga gcaagagcag gaggctggag aacctgatcg cccagctgcc cggcgagaag  1500
aagaacggcc tgttcggcaa cctgatcgcc ctgagcctgg gcctgacccc caacttcaag  1560
agcaacttcg acctggccga ggacgccaag ctgcagctga gcaaggacac ctacgacgac  1620
gacctggaca acctgctggc ccagatcggc gaccagtacg ccgacctgtt cctggccgcc  1680
aagaacctga gcgacgccat cctgctgagc gacatcctga gggtgaacac cgagatcacc  1740
aaggcccccc tgagcgccag catgatcaag aggtacgacg agcaccacca ggacctgacc  1800
ctgctgaagg ccctggtgag gcagcagctg cccgagaagt acaaggagat cttcttcgac  1860
cagagcaaga acggctacgc cggctacatc gacggcggcg ccagccagga ggagttctac  1920
aagttcatca agcccatcct ggagaagatg gacggcaccg aggagctgct ggtgaagctg  1980
aacagggagg acctgctgag gaagcagagg accttcgaca acggcagcat cccccaccag  2040
atccacctgg gcgagctgca cgccatcctg aggaggcagg aggacttcta ccccttcctg  2100
aaggacaaca gggagaagat cgagaagatc ctgaccttca ggatccccta ctacgtgggc  2160
cccctggcca ggggcaacag caggtcgcct ggatgaccag gaagagcgag gagaccatca  2220
ccccctggaa cttcgaggag gtggtggaca agggcgccag cgcccagagc ttcatcgaga  2280
ggatgaccaa cttcgacaag aacctgccca acgagaaggt gctgcccaag cacagcctgc  2340
tgtacgagta cttcaccgtg tacaacgagc tgaccaaggt gaagtacgtg accgagggca  2400
tgaggaagcc cgccttcctg agcggcgagc agaagaaggc catcgtggac ctgctgttca  2460
agaccaacag gaaggtgacc gtgaagcagc tgaaggagga ctacttcaag aagatcgagt  2520
gcttcgacag cgtggagatc agcggcgtgg aggacaggtt caacgccagc ctgggcacct  2580
accacgacct gctgaagatc atcaaggaca aggacttcct ggacaacgag gagaacgagg  2640
acatcctgga ggacatcgtg ctgaccctga ccctgttcga ggacagggag atgatcgagg  2700
agaggctgaa gacctacgcc cacctgttcg acgacaaggt gatgaagcag ctgaagagga  2760
ggaggtacac cggctggggc aggctgagca ggaagctgat caacggcatc agggacaagc  2820
agagcggcaa gaccatcctg gacttcctga agagcgacgg cttcgccaac aggaacttca  2880
tgcagctgat ccacgacgac agcctgacct tcaaggagga catccagaag gcccaggtga  2940
gcggccaggg cgacagcctg cacgagcaca tcgccaacct ggccggcagc cccgccatca  3000
agaagggcat cctgcagacc gtgaaggtgg tggacgagct ggtgaaggtg atgggcaggc  3060
acaagcccga gaacatcgtg atcgagatgg ccagggagaa ccagaccacc cagaagggcc  3120
agaagaacag cagggagagg atgaagagga tcgaggaggg catcaaggag ctgggcagcc  3180
agatcctgaa ggagcacccc gtggagaaca cccagctgca gaacgagaag ctgtacctgt  3240
actacctgca gaacggcagg gacatgtacg tggaccagga gctggacatc aacaggctga  3300
gcgactacga cgtggaccac atcgtgcccc agagcttcct gaaggacgac agcatcgaca  3360
acaaggtgct gaccaggagc gacaagaaca ggggcaagag cgacaacgtg cccagcgagg  3420
aggtggtgaa gaagatgaag aactactgga ggcagctgct gaacgccaag ctgatcaccc  3480
agaggaagtt cgacaacctg accaaggccg agaggggcgg cctgagcgag ctggacaagg  3540
ccggcttcat caagaggcag ctggtggaga ccaggcagat caccaagcac gtggcccaga  3600
tcctggacag caggatgaac accaagtacg acgagaacga caagctgatc agggaggtga  3660
aggtgatcac cctgaagagc aagctggtga gcgacttcag gaaggacttc cagttctaca  3720
aggtgaggga gatcaacaac taccaccacg cccacgacgc ctacctgaac gccgtggtgg  3780
gcaccgccct gatcaagaag taccccaagc tggagagcga gttcgtgtac ggcgactaca  3840
aggtgtacga cgtgaggaag atgatcgcca agagcgagca ggagatcggc aaggccaccg  3900
ccaagtactt cttctacagc aacatcatga acttcttcaa gaccgagatc accctggcca  3960
acggcgagat caggaagagg cccctgatcg agaccaacgg cgagaccggc gagatcgtgt  4020
gggacaaggg cagggacttc gccaccgtga ggaaggtgct gagcatgccc caggtgaaca  4080
tcgtgaagaa gaccgaggtg cagaccggcg gcttcagcaa ggagagcatc ctgcccaaga  4140
ggaacagcga caagctgatc gccaggaaga aggactggga ccccaagaag tacggcggct  4200
tcgacagccc caccgtggcc tacagcgtgc tggtggtggc caaggtggag aagggcaaga  4260
gcaagaagct gaagagcgtg aaggagctgc tgggcatcac catcatggag aggagcagct  4320
tcgagaagaa ccccatcgac ttcctggagg ccaagggcta caaggaggtg aagaaggacc  4380
tgatcatcaa gctgcccaag tacagcctgt tcgagctgga gaacggcagg aagaggatgc  4440
tggccagcgc cggcgagctg cagaagggca acgagctggc cctgcccagc aagtacgtga  4500
acttcctgta cctggccagc cactacgaga agctgaaggg cagccccgag gacaacgagc  4560
agaagcagct gttcgtggag cagcacaagc actacctgga cgagatcatc gagcagatca  4620
gcgagttcag caagagggtg atcctggccg acgccaacct ggacaaggtg ctgagcgcct  4680
acaacaagca cagggacaag cccatcaggg agcaggccga gaacatcatc cacctgttca  4740
ccctgaccaa cctgggcgcc cccgccgcct tcaagtactt cgacaccacc atcgacagga  4800
agaggtacac cagcaccaag gaggtgctgg acgccaccct gatccaccag agcatcaccg  4860
gcctgtacga gaccaggatc gacctgagcc agctgggcgg cgacggcccc ggcgagaacc  4920
tgtacttcca gggcgccggc gactacaagg acgacgacga caagggctga taa         4973

SEQ ID NO: 24          moltype = DNA  length = 20
FEATURE                Location/Qualifiers
source                 1..20
                       mol_type = other DNA
                       organism = synthetic construct
SEQUENCE: 24
gtctcagcct cgcgctatgc                                              20
```

UTILIZATION OF GENE TARGETING ANTIBODY FUSION PROTEINS TO PERFORM IN VIVO THERAPEUTIC GENE EDITING

BACKGROUND

This application is a continuation claiming the benefit of priority to International Application No. PCT/US2023/075304 filed Sep. 28, 2023, which claims priority to and the benefit of U.S. Provisional Patent Application Ser. No. 63/377,618, filed Sep. 29, 2022, and also claims priority to and the benefit of U.S. Provisional Patent Application Ser. No. 63/377,616, filed Sep. 29, 2022, all of which applications are incorporated by reference herein in their entireties.

SEQUENCE LISTING

The instant application contains a Sequence Listing which has been submitted electronically in XML file format and is hereby incorporated by reference in its entirety. Said XML copy, created on Apr. 7, 2026, is named BAYM_P0380US_SL.xml and is 35,322 bytes in size.

I. Technical Field

Embodiments of the disclosure concern at least the fields of cell biology, molecular biology, immunology, and medicine, including cancer medicine, inborn errors of metabolism, hematopoietic diseases, and/or genetic diseases affecting liver function.

II. Background

Immunotherapies for cancer and other diseases are showing promising advances in the field of medicine. Methods and compositions to specifically take action at a desired target are in demand, including for activity directed to the outside of cells of interest and within its nucleus. The subject matter of the present disclosure satisfies such a longfelt need in the art.

SUMMARY

Embodiments of the disclosure include a fusion protein ribonucleotide complex comprising a fusion protein and at least one RNA, wherein the fusion protein comprises at least one antibody or antibody fragment; and at least one RNA-guided DNA endonuclease.

Embodiments of the disclosure include a fusion protein ribonucleotide complex comprising a fusion protein and at least one RNA targeting SRC-3, wherein the fusion protein comprises at least one antibody or antibody fragment (such as an scFv); and at least one RNA-guided DNA endonuclease.

The RNA-guided DNA endonuclease may be Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or a functional derivative thereof. In specific embodiments, the RNA comprises sequence complementary to one or more polynucleotides target of interest. In some embodiments, the RNA comprises sequence complementary to SRC-3. In some embodiments, the fusion protein further comprises a linker domain between the antibody, or antibody fragment, and the RNA-guided DNA endonuclease. The fusion protein may further comprise one or more purification tags, such as one that comprises a His tag, FLAG-tag, HA, calmodulin binding peptide, cellulose binding domain, chitin biding domain, albumin-binding protein, AU1 epitope, AU5 epitope, biotin-carboxy carrier protein, galatose-binding protein, glutathione S-transferase, Halotag, streptavidin-binding peptide, or by tamden affinity purification. In some embodiments, the fusion protein further comprises one or more proteases, such as Tobacco Etch Virus (TEV) protease, Enterokinase, PreScission protease, Enteropeptidase, thrombin, 3C protease, or Factor Xa. In various embodiments, the antibody fragment is an scFv. In specific embodiments, the antibody or antibody fragment targets a cell surface protein or a cancer antigen. In particular cases, the antibody or antibody fragment targets CD25, CD19, CD4, HER2, PD-1, CTLA-4, TGFBR, or EGFR. In some embodiments, the one or more polynucleotides target of interest is an oncogene, Tumor suppressor, growth or proliferation related gene, invasion or metastasis related gene, or a gene involved epithelial to mesenchymal transition. Examples of one or more polynucleotides target of interest include PTEN, PIK3CA, TP53, VIM, TWIST1, ESR1, or MYC.

Embodiments of the disclosure include polynucleotides encoding the fusion protein, expression constructs comprising at least one nucleotide sequence encoding the fusion protein, the RNA, cells that express any part of the complex, and/or therapeutic compositions comprising the complex that may be housed in a pharmaceutically acceptable carrier.

Embodiments of the disclosure include methods of treating an individual comprising administering to the individual a therapeutically effective amount of the complex, the polynucleotide, the expression construct, the therapeutic composition, and/or cells that produce part or all of the complex. In some embodiments, the individual has, or is suspected of having, a cancer, such as breast cancer, ovarian cancer, endometrial cancer, prostate cancer, gastric cancer, multiple myeloma, thyroid cancer, pancreatic cancer, tumors of the bone marrow, T or B cell malignancies, leukemia, lymphoma, blastoma, myeloma, lung cancer, cancer of the peritoneum, gastric or stomach cancer, cervical cancer, liver cancer, bladder cancer, colon cancer, colorectal cancer, uterine carcinoma, salivary gland carcinoma, kidney or renal cancer, vulval cancer, head and neck cancer, or melanoma. In specific embodiments, the individual has, or is suspected of having, a cancer, including a cancer that comprises SRC-3 expressing cells. In some embodiments, the individual has, or is suspected of having, an inflammatory disease, such as an allergy, asthma, an autoimmune disease, coeliac disease, glomerulonephritis, hepatitis, inflammatory bowel disease, preperfusion injury, transplant rejection, ankylosing spondylitis (AS), gout, myositis, rheumatoid arthritis, scleroderma, Sjogren's Syndrome, systemic lupus Erythematosus, pelvic inflammatory disease, or vasculitis. In some embodiments, the individual has, or is suspected of having an inherited disorder, optionally an in-born error of metabolism disease, such as glycogen storage disease, G6PD deficiency, phenylketonuria, maple syrup urine disease, glutaric acidemia type 1, carbamoyl phosphate synthetase I deficiency, alkaptonuria, combined malonic and methylmalonic aciduria, 2-hydroxyglutaric acidurias, medium-chain acyl-coenzyme A dehydrogenase deficiency, acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann-Pick disease.

In specific embodiments, cells that produce part or all of the complex are immune cells, such as T cells, natural killer (NK cells), NK T cells, B cells, macrophages, dendritic cells, or a mixture thereof.

In particular embodiments, administration of a therapeutically effective amount of the complex, the polynucleotide, the expression construct, the therapeutic composition, and/or cells that produce part or all of the complex to the individual induces SRC-3 disruption in immune cells, such as T cells, natural killer (NK cells), NK T cells, B cells, macrophages, dendritic cells, or a mixture thereof. The immune cells may comprise CD4+ cells, CD25+ cells, and/or FOXP3+ cells.

In some embodiments, the administration is intravenously, intraperitoneally, intraarterially, topically, by inhalation, intramuscularly, intrasternally, by intraarticular injection, or by infusion. Some methods include further administering a second therapeutic intervention, such as surgery, radiation, chemotherapy, hormone therapy, drug therapy, protein therapy, immunotherapy, or a combination thereof. The second therapeutic intervention may be administered substantially concurrently or substantially consecutively with the complex, the polynucleotide, the expression construct, the therapeutic composition and/or with cells that produce part or all of the complex.

The complex, the polynucleotide, the expression construct, the therapeutic composition, and/or cells that produce part or all of the complex may be administered intravenously, intraperitoneally, intraarterially, topically, by inhalation, intramuscularly, intrasternally, by intraarticular injection, or by infusion. In some cases, the method further comprises administering a second therapeutic intervention, such as surgery, radiation, chemotherapy, hormone therapy, drug therapy, protein therapy, immunotherapy, or a combination thereof. The second therapeutic intervention may be administered substantially concurrently or substantially consecutively with the complex, the polynucleotide, the expression construct, the therapeutic composition and/or cells that produce part or all of the complex.

Embodiments of the disclosure include methods of manufacturing the complex comprising the steps of a. expressing the fusion protein; b. expressing the RNA; c. contacting the fusion protein with the RNA. The method may further comprise purifying the fusion protein, such as by affinity chromatography. The method may further comprise purifying the RNA.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 2 shows a diagram representing one example of the production of a CRISPR/Cas9/CD25 targeting antibody/SRC-3 gene targeting sgRNA polypeptide/ribonucleotide complex expressed in *E. coli* or other bacteria, yeast-based systems including *Saccharomyces cerevisiae, Pichia pastoris, Hansenula polymorpha, Yarrowia lipolytica, Arxula adeninivorans, Kluyveromyces lactis*, and *Schizosaccharomyces pombe*, T7 RNA polymerase coupled translation (TNT) systems, or in mammalian cell expression systems, such as HEK293T or other cell lines. The SRC-3 gene is merely one example.

FIG. 3 shows a diagram representing one example of a route of administration of a CRISPR/Cas9/CD25 targeting antibody/SRC-3 gene targeting sgRNA polypeptide/ribonucleotide complex, such as for therapeutic use of any kind. The SRC-3 gene is merely one example.

DETAILED DESCRIPTION

I. Definitions

Figure 1:
FIG. 1 shows schematic and sequence details representing the construction of one example of a CRISPR/Cas9/targeting antibody fusion protein, which, in some embodiments, is designed as an intravenously injectable for in vivo gene deletion. The modular components that comprise this fusion protein, or cDNA expressing same, in some embodiments include a histidine tag (6His tag); a cell penetrating peptide (CPP); a single-chain variable fragment (scFv) that, in some embodiments, binds to the CD25 (Gene Symbol: IL2RA) protein expressed on the surface of Tregs; a CRISPR/Cas nuclease protein; a Tobacco Etch Virus (TEV) protease; and FLAG-tag that are linked together to be expressed as a single polypeptide through various linker domains.
Figure 1:
Figure 1:
Figure 1:
Figure 1:
Figure 1:

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the compositions and/or steps disclosed throughout the specification. Compositions and methods "consisting essentially of" any of the compositions and/or steps disclosed limits the scope of the subject matter to the specified materials or steps which do not materially affect the basic and novel characteristic of the subject matter of the disclosure.

As used herein, a "protein" or "polypeptide" refers to a molecule comprising at least five amino acid residues. As used herein, the term "wild-type" refers to the endogenous version of a molecule that occurs naturally in an organism. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, a “disruption” or “alteration” of a gene refers to the elimination, reduction, or elevation of expression of one or more gene products encoded by the gene in a cell, compared to the level of expression of the gene product in the absence of the alteration. Exemplary gene products include mRNA and protein products encoded by the gene. Alteration in some cases is transient or reversible and in other cases is permanent. Alteration, in some cases, is of a functional or full length protein or mRNA, despite the fact that a truncated or non-functional product may be produced.

As used herein, “pharmaceutically acceptable carrier” includes any and all aqueous solvents (e.g., water, alcoholic/aqueous solutions, saline solutions, parenteral vehicles, such as sodium chloride, Ringer’s dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The terms “subject” or “individual” as used herein, generally refer to an individual in need of treatment. The subject can be any animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as one or more cancers. The subject may be undergoing or having undergone cancer treatment. The term “individual” may be used interchangeably, in at least some embodiments. The “subject” or “individual”, as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (e.g., children) and infants and includes in utero individuals. The individual may be of any gender or race or ethnicity.

“Treating” or treatment of a disease or condition refers to executing a protocol, which may include administering one or more compositions to an individual, in an effort to alleviate signs or symptoms of the disease, including cancer, inborn errors of metabolism, hematopoietic diseases and genetic diseases affecting liver function. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, “treating” or “treatment” may include “preventing” or “prevention” of disease or undesirable condition. In addition, “treating” or “treatment” does not require complete alleviation of signs or symptoms, does not require a cure, and specifically includes protocols that have only a marginal effect on the patient.

The term “therapeutic benefit” or “therapeutically effective” as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, a reduction in the size of a tumor, a reduction in the invasiveness of a tumor, reduction in the growth rate of the cancer, prevention of metastasis, or delay in onset of metastasis. Treatment of cancer may also refer to prolonging survival of a subject with cancer.

The term “functionally equivalent codon” is used herein to refer to codons that encode the same amino acid, such as the six different codons for arginine. Also considered are “neutral substitutions” or “neutral mutations” which refers to a change in the codon or codons that encode biologically equivalent amino acids.

The term “polynucleotide” refers to a nucleic acid molecule that either is recombinant or has been isolated from total genomic nucleic acid. Included within the term “polynucleotide” are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term “gene,” “polynucleotide,” or “nucleic acid” is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein.

As used herein “sgRNA”, “short guide RNA”, “small guide RNA”, “single guide RNA”, “guide RNA” and “gRNA” are used interchangeably.

It is contemplated that any embodiment discussed in this specification can be implemented with respect to any method or composition of the disclosure, and vice versa. Furthermore, compositions of the disclosure can be used to achieve methods of the disclosure.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

II. General Embodiments

The present disclosure is directed to systems, methods, and compositions for research purposes or for treating, delaying progression of, delaying onset of, or reducing the risk of a disease. In various embodiments, the disease may be a cancer of any kind; inherited disorders (such as Sickle cell disease; Beta thalassemia, retinal dystrophies); inborn errors of metabolism; hematopoietic diseases; neurodegenerative diseases (such as AML); inflammatory diseases; and/or genetic diseases, e.g., those affecting liver function. Certain embodiments concern the specific modification of one or more genes in cells of any kind within the human body. The genetic modification may result in the loss and/or alteration of expression of at least one target gene. In specific embodiments, the genetic modification is targeted to specific cells based on targeting of at least one surface antigen of the cells. The genetic modification may result in the loss and/or alteration of expression of endogenous SRC-3. In specific embodiments, the genetic modification is targeted to specific cells based on at least one surface antigen of the cells. The surface antigen, in some embodiments, is CD25, CD4, and/or FOXP3.

The present disclosure, in certain embodiments, encompasses methods and compositions that exploit cell surface proteins to deliver synthetically designed CRISPR/Cas9/targeting antibody/gene targeting sgRNA fusion protein/ribonucleotide complexes to the cell that are capable of specifically disrupting one or more target genes of the cell. In specific embodiments, the protein/ribonucleotide complex is able to be administered in any form to an individual in need thereof. The complexes may target any cell or population of cells that have a specific, targetable surface antigen, including immune cells such as T cells, NK cells, NK T cells, B cells, macrophages, dendritic cells, or a mixture thereof. Such complexes may allow for the avoidance of ex vivo gene targeting of Tregs, including through leukapheresis.

In certain embodiments, one or more particular genes are desired to be disrupted in one or more particular types of cells. The complex may comprise an antibody or antibody fragment that brings the CRISPR/sgRNA components to the cells via the cell surface proteins, the cells in which a gene of interest is desired to be disrupted by the CRISPR/sgRNA. In certain embodiments, the targeting antibody or antibody fragment targets one or more cell surface proteins, thereby delivering the CRISPR complex to the cell and allowing for the disruption of the target gene in cells contacted with the complex. Additional embodiments of this disclosure include the substitution of one cell targeting antibody with any other antibody to target other cell surface antigens. Another additional embodiment includes the substitution of a particular gene targeting sgRNA with any other sgRNA designed to target other genes or regions in the genome. One skilled in the art would recognize that the modular components of the complexes may be interchanged with other functional components. For example, the scFv of a complex described herein, such as an scFv targeting a cancer antigen, may be exchanged for an scFv targeting a different surface antigen, including any surface antigen encompassed herein. In another example, the sgRNA of a complex described herein, such as an sgRNA targeting a gene of interest, may be exchanged for an sgRNA targeting a different gene, including any gene described herein. In certain embodiments, 1, 2, 3, 4, 5, 6, 7, 8, 9, 10, or more sgRNAs are utilized to target 1, 2, 3, 4, 5, 6, 7, 8, 9, 10, or more genes.

The present disclosure, in certain embodiments, encompasses methods and compositions to exploit cell surface proteins to deliver synthetically designed CRISPR/Cas9/targeting antibody/SRC-3 targeting sgRNA fusion protein/ribonucleotide complexes capable of specifically disrupting SRC-3. (Gene Symbol: NCOA3) In certain embodiments, the complex is able to be administered in any form to an individual in need thereof. The complexes may target any cell or population of cells that have a specific, targetable surface antigen, including immune cells such as T cells, NK cells, NK T cells, B cells, macrophages, dendritic cells, or a mixture thereof. Such complexes may allow for the avoidance of ex vivo gene targeting of Tregs, including through leukapheresis. In certain embodiments the targeting antibody targets CD25, allowing for the disruption of the target gene in cells contacted with the complex. Additional embodiments of this disclosure include the substitution of one cell targeting antibody with any other antibody to target other cell surface antigens. One skilled in the art would recognize that the modular components of the complexes may be interchanged with other functional components. For example, the scFv of a complex described herein, such as an scFv targeting CD25, may be exchanged for an scFv targeting a different surface antigen, including any surface antigen described herein.

In some embodiments, there is a fusion protein ribonucleotide complex comprising a fusion protein and at least one short guide RNA (sgRNA) (e.g., at least one SRC-3 short guide RNA (sgRNA)), wherein the fusion protein comprises at least one antibody or antibody fragment; and at least one RNA-guided DNA endonuclease. In specific embodiments, two or more antibodies or antibody fragments are utilized to enhance the ability to target specific cells having two different surface proteins of interest. In additional embodiments or alternative embodiments, the complex comprises two or more different sgRNAs that target the same gene or different genes.

In some embodiments, expression of a gene (including at least SRC-3) in a cell is disrupted by contacting the cell with a complex described herein. In some embodiments herein, gene activity or function, as opposed to expression, is disrupted. Gene disruption or alteration may be induced by artificial methods, i.e., by addition or introduction of an RNA-guided DNA endonuclease enzyme (such as CRISPR associated protein 9 (Cas9)), any CRISPR proteins, complexes, or compositions at the DNA level. Methods for gene alteration herein include any protein that interacts with DNA in a nucleotide-specific manner including any CRISPR protein, such as nuclease-dead CRISPR variants, zinc finger nucleases, and TALENs, or other gene editing techniques that result in targeted gene inactivation or alteration including by induction of breaks and/or homologous recombination or through chemical modification of DNA or associated chromatin proteins. The CRISPR protein may comprise Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2, which is incorporated by reference herein. Modifications may include insertions, mutations, and/or deletions to DNA, DNA methylation, and/or post-translational modifications to histone associated with the targeted DNA. The disruptions or alterations typically result in the repression and/or complete absence of expression of a normal or "wild type" product encoded by the gene, such as SRC-3. In some embodiments, gene disruptions or alterations are insertions, frameshift and missense mutations, deletions, knock-in, and knock-out of the gene or part of the gene, including deletions of the entire gene. Such alterations can occur in the coding region, e.g., in one or more exons, resulting in the inability to produce a full-length product, functional product, or any product, such as by insertion of a stop codon. Such alterations may also occur by alterations in the promoter or enhancer or other region affecting activation of transcription, so as to prevent transcription of the gene. Gene disruptions or alterations include gene targeting, including targeted gene inactivation by homologous recombination.

Current cell-targeting immune checkpoint inhibitors are mostly focused on surface proteins (receptors) that disrupt their cell surface interactions with other immune cells. Embodiments of the present disclosure distinguish from cell surface interactions by ultimately targeting a gene target. Specific embodiments relate to immune cells and concern an approach to target a particular gene in immune cells in vivo by utilizing a CRISPR/Cas9/surface protein-targeting antibody/gene of interest sgRNA fusion protein ribonucleotide complex to generate genetically modified cells, such as for the treatment of cancer, inherited diseases, inflammatory disorders, neurodegenerative diseases, inborn errors of metabolism, hematopoietic diseases, and/or genetic diseases, such as those affecting liver function. Thus, the present disclosure, in certain embodiments, provides a unique way to support immune-system based tumor eradication without the need for ex vivo handling of immune cells. In certain embodiments, the fusion protein ribonucleotide complex targets other genes to effect a response in the cell. In certain embodiments, the fusion protein ribonucleotide complex targets other surface antigens to effect a response in cell types that are not Tregs.

Embodiments of the present disclosure distinguish from cell surface interactions by targeting SRC-3 as a Treg gene target. SRC-3 is a nuclear protein that functions to regulate Treg nuclear gene expression programs. As a consequence of its role as a transcriptional master regulator, ablation of SRC-3 in a mouse genetic model can modulate Treg function in a way that promotes tumor eradication while avoiding the otherwise severe side effects that are frequently observed with established immune checkpoint inhibitors. Specific embodiments concern an approach to target the SRC-3 gene in immune cells in vivo by utilizing a CRISPR/Cas9/targeting antibody/SRC-3 gene sgRNA fusion protein ribonucleotide complex to generate genetically modified Treg cells, such as for the treatment of cancer, inherited diseases, inflammatory disorders, neurodegenerative diseases, inborn errors of metabolism, hematopoietic diseases, and/or genetic diseases, such as those affecting liver function. Thus, the present disclosure, in certain embodiments, provides a unique way to support immune-system based tumor eradication without the need for ex vivo handling of immune cells. In certain embodiments, the fusion protein ribonucleotide complex targets other genes to effect a response in the cell. In certain embodiments, the fusion protein ribonucleotide complex targets other surface antigens to effect a response in cells types that are not Tregs.

Certain embodiments concern the use of the fusion protein ribonucleotide complexes to treat or prevent other diseases including inborn errors of metabolism, hematopoietic diseases, genetic diseases, liver diseases, and the like.

Certain embodiments concern methods and compositions for effective therapy, including cancer therapy, that avoids severe effects for the treated individual. In particular embodiments, the therapy comprises modification of immune cells residing within the body. In certain embodiments, immune cells are modified in an ex vivo manner, which may be administered to an individual, including an individual with cancer. The immune cells in particular embodiments are of a specific type of immune cells, and their modification may be such that the standard function of the modified cells are not deleteriously impacted. Certain embodiments also concern the ability of a CRISPR/Cas9/targeting antibody/SRC-3 gene targeting small guide sgRNA fusion protein/ribonucleotide complex to specifically target proteins that express the CD25 protein on their cell surface. The CD25 scFv portion of the CRISPR/Cas9/targeting antibody/SRC-3 gene targeting small guide RNA (sgRNA) fusion protein/ribonucleotide complex is designed to bind to cell surface expressed CD25 on Tregs, in various embodiments.

Particular embodiments of the present disclosure encompass SRC-3 as a key target in immune cells, including at least Tregs. With respect to Tregs, the specific compartment-specific disruption may lead to tumor eradication, including in a breast cancer tumor model. A key difference that differentiates the present strategy of disrupting SRC-3, in certain embodiments, in Tregs from other immune checkpoint inhibitors is that SRC-3 is a nuclear protein, and certain modifications in the present disclosure modulate the function of Tregs without losing all activity for the Tregs, which in other cases could result in severe side effects. Furthermore, the present disclosure establishes an approach to specifically ablate SRC-3 in Treg cells in vivo using CRISPR-based gene targeting. In particular embodiments applied to human CD4+ lymphocytes, for example, the present disclosure provides methods for in vivo Treg-based therapeutics for the treatment of cancers.

Certain embodiments concern an engineered cell, or a plurality thereof, comprising disruption of one or more endogenous genes, such as SRC-3. The immune cell may be any immune effector cell. In some embodiments, the disruption is further defined as the immune cell being genetically modified to have reduced expression of the endogenous gene(s) or having essentially no expression of the endogenous gene(s). In certain embodiments, the immune cell is engineered using one or more guide RNAs and RNA-guided DNA endonuclease or a protein that contains sequences that express all or part of the enzyme. In some embodiments, the immune cell is autologous with respect to an individual. In some embodiments, the immune cell is allogeneic with respect to an individual.

In various embodiments, the immune cell may be any immune effector cell, including a T cell. The immune cell may be a T regulatory cell, in some cases. The immune cell may be CD4+, CD25+, and/or FOXP3+. In some embodiments, the disruption is further defined as the immune cell being genetically modified to have elevated or reduced expression of SRC-3 or having essentially no expression of SRC-3. In certain embodiments, the immune cell is engineered using one or more guide RNAs and a Cas9 enzyme or a protein that contains sequences that express all or part of the Cas9 enzyme. In some embodiments, the immune cell is autologous with respect to an individual. In some embodiments, the immune cell is allogeneic with respect to an individual.

Embodiments herein concern compositions comprising any cell described herein and a CRISPR/Cas9/targeted antibody/gene targeting sgRNA fusion protein/ribonucleotide complex. In some embodiments, the cells and complexes interact in the body (in vitro) or ex vivo.

Embodiments herein concern cells expressing the CD25 surface protein that can be bound by a CD25 targeting scFV antibody. Embodiments herein concern cells expressing a membrane protein that can be bound by a monoclonal or scFV antibody.

Embodiments herein concern compositions comprising any cell described herein and a CRISPR/Cas9/targeted antibody/SRC-3 gene targeting sgRNA fusion protein/ribonucleotide complex. In some embodiments, the cells and complexes interact in the body (in vitro) or ex vivo.

Certain embodiments concern methods of treating cancer in an individual, comprising the step of administering to the individual a therapeutically effective amount of any composition described herein. In some embodiments, the cancer expresses one or more deleterious genes that are targeted by compositions encompassed herein for therapeutic purpose.

In some embodiments, the individual is administered a therapeutically effective amount of an additional therapy, including in the case of cancer one or more additional cancer therapies. The additional cancer therapy may comprise surgery, radiation, chemotherapy, hormone therapy, drug therapy, protein therapy, immunotherapy, or a combination thereof. In some embodiments, the cells and/or complexes and the additional cancer therapy are administered to the individual at substantially the same time or at different times. The cells and/or complexes and the additional cancer therapy may be in the same formulation or in different formulations.

In some embodiments, the cells and/or complexes are administered intravenously, intraperitoneally, intraarterially, topically, by inhalation, intramuscularly, intrasternally, by intraarticular injection, or by infusion. In some embodiments, the T cells, Tregs, or other cells are obtained from the spleen, bone marrow, blood, plasma, tissues or a combination thereof.

III. Immune Cells

In the present disclosure, certain cells, including immune cells, are modified to disrupt expression of one or more endogenous genes, that then allows the cells to be effective for treating a disease, including cancer, in a recipient individual receiving the modified cells. In various embodiments, certain cells, including immune cells, are modified to disrupt expression of endogenous SRC-3 that then allows the cells to be effective for treating a disease, including cancer, in a recipient individual receiving the modified cells. Although cells may be of any kind, in specific embodiments the cells, of any kind, express one or more particular surface proteins on their cell surface.

Any cell that expresses a particular surface protein of interest may be utilized and/or modified in methods and compositions of the disclosure. The term "T cell" refers to T lymphocytes, and includes, but is not limited to, $CD4^+$ T cells, $CD8^+$ T cells, $\gamma$: $\delta^+$ T cells, or NK T cells. $CD4^+$ T cells include $T_H0$, $T_H1$ and $T_H2$ cells, as well as regulatory T cells ($T_{reg}$). There are at least three types of regulatory T cells: $CD4^+$ $CD25^+$ $T_{reg}$, CD25 $T_H3$ $T_{reg}$, and CD25 $T_R1$ $T_{reg}$. "Cytotoxic T cell" refers to a T cell that can kill another cell. The majority of cytotoxic T cells are $CD8^+$ MHC class I-restricted T cells, however some cytotoxic T cells are $CD4^+$. In particular embodiments, the T cell is $CD4^+$.

Any cells of interest herein may be targeted through any cell surface marker and by any type of antibody, ligand or other protein with affinity for a cell surface marker, in some cases. In particular embodiments, the cells are CD4+, CD25+, and/or FOXP3+, CTL-associated protein 4 (CTLA4)+, C—C chemokine receptor type 7 (CCR7)+, and/or CD62 antigen ligand (CD62L)+. Also included here are cells, which may be Tregs, that through disruption of the SRC-3 gene, subsequently cease to express FOXP3, CD25 and/or CD4.

In some embodiments that utilize ex vivo treatment with the CRISPR/Cas9/targeting antibody/gene targeting sgRNA fusion protein, CD4+ immune cells, including CD4+ T cells, are targeted with methods and compositions of the disclosure to disrupt expression of a gene, and in at least some cases, the cells may be further selected therefrom to be used as the therapeutic cells. In some embodiments that utilize ex vivo treatment with the CRISPR/Cas9/targeting antibody/SRC-3 gene targeting sgRNA fusion protein, CD4+ immune cells, including CD4+ T cells, are targeted with methods and compositions of the disclosure to disrupt expression of a gene, such as SRC-3, and in at least some cases, the cells may be further selected therefrom to be used as the therapeutic cells. In alternative cases, a variety of CD4+ cells are modified and collectively used as the therapeutic cells without a further step of isolating the cells.

In cases wherein cells, such as immune cells, are utilized for ex vivo modification, the source of the cells may be of any suitable source, including the spleen, bone marrow, blood, plasma, or a combination thereof. In some cases, the cells are obtained commercially. In certain embodiments, the cells may be autologous with respect to a recipient individual or allogeneic with respect to a recipient individual. The cells may be manipulated prior to the step of engineering the cells to have the disruption of the desired gene, such as SRC-3. In some cases, the cells are processed from a source, such as to remove undesired constituents. The cells may be exposed to one or more compositions that enhance its activity in an individual prior to use therein, such as one or more agents that target the desired gene, or other compositions.

In particular embodiments, the immune cells that are engineered to have disruption of a gene (such as SRC-3) include B cells. In particular embodiments, the disrupted B cells, such as through a scFV in the CRISPR/Cas9/targeting antibody/gene targeting sgRNA fusion protein/ribonucleotide complex are utilized for any medical condition for which the B cells would be effective, but in specific embodiments the modified B cells are utilized for treatment of one or more inflammatory diseases or treatment of cancer of any kind, including at least B cell lymphomas and those cancers listed elsewhere herein, for example. The B cells may be engineered ex vivo to disrupt expression of an endogenous gene (such as SRC-3) in the B cells. In some cases, the engineered B cells are exposed to one or more agents including TGF-β or tumor-specific antigens that facilitate efficacy of the B cells once administered to the individual in need.

In particular embodiments, the engineered B cells, including those lacking expression of a particular endogenous gene (such as SRC-3) or having reduced expression of a particular endogenous gene compared to non-engineered B cells, are administered in an effective amount to an individual having or at risk for having one or more inflammatory diseases.

Although the inflammatory disease may be of any kind, in specific embodiments the disease is allergy, asthma, autoimmune diseases, coeliac disease, glomerulonephritis, hepatitis, inflammatory bowel disease, preperfusion injury, transplant rejection, ankylosing spondylitis (AS), gout; myositis, rheumatoid arthritis, scleroderma, Sjogren's Syndrome, systemic lupus Erythematosus (SLE, Lupus), pelvic inflammatory disease, or vasculitis, merely as examples. The B cell treatment may reduce or delay the severity of the disease, delay the onset of the disease, improve one or more symptoms of the disease, and so forth.

IV. Gene Disruption

In various embodiments, one or more endogenous genes (such as SRC-3) are disrupted, such as through a disruption in expression, in cells, and the component(s) utilized for such disruption are transported to the cells based on a moiety that binds the surface of the cell, such as through a cell surface protein. The cells may be utilized for research and/or therapeutic purposes, and the gene of interest may be selected based on a desired use of the cells. In some embodiments, the altered gene expression (such as SRC-3) is carried out by effecting a disruption in the gene, such as a knock-out, insertion, missense or frameshift mutation, such as biallelic frameshift mutation, deletion of all or part of the gene, e.g., one or more exons or portions therefore, and/or knock-in. For example, the altered gene expression can be effected by sequence-specific or targeted nucleases including RNA-guided nucleases such as CRISPR/Cas9 or any variant thereof, or DNA-binding targeted nucleases such as zinc finger nucleases (ZFN) and transcription activator-like effector nucleases (TALENs). In some embodiments, the sequence-specific or targeted nuclease, or fusion protein or complex comprising the sequence-specific or targeted nuclease, is specifically designed to be targeted to the sequence of the target gene or a portion thereof. Examples of genes to be disrupted include at least the following: SRC-3, CD19, CD319/CS1, ROR1, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, WT-1, EGFRvIII, TRAIL/DR4, VEGFR2, fibroblast growth factor receptors (FGFR1, FGFR2, FGFR3, FGFR4), E-cadherin, collagen-binding integrins ($\alpha1\beta1$, $\alpha2\beta1$, $\alpha10\beta1$, $\alpha11\beta1$), and/or leukocyte-binding integrins (e.g., $\alpha L\beta2$, $\alpha M\beta2$, $\alpha4\beta1$).

In some embodiments, the alteration of the expression, activity, and/or function of the gene is carried out by disrupting the gene. In some aspects, the gene is modified so that its expression is reduced by at least at or about 20, 30, or 40%, generally at least at or about 50, 60, 70, 80, 90, 95%, 96%, 97%, 98%, 99%, or more as compared to the expression in the absence of the gene modification or in the absence of the components introduced to effect the modification.

In some embodiments, the alteration is transient or reversible, such that expression of the gene is restored at a later time. In other embodiments, the alteration is not reversible or transient. In some embodiments, the alteration is permanent.

In some embodiments, gene alteration (such as SRC-3) is carried out by induction of one or more double-stranded breaks and/or one or more single-stranded breaks in the gene. The double-stranded or single-stranded breaks may be done in a targeted manner. In some embodiments, the double-stranded or single-stranded breaks are made by a nuclease, e.g. an endonuclease, such as a gene-targeted nuclease. In some aspects, the breaks are induced in the coding region of the gene, e.g. in an exon. For example, in some embodiments, the induction occurs near the N-terminal portion of the gene coding region, e.g. in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene (such as SRC-3). For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in disruption of the expression, activity, and/or function of the gene. In some embodiments, nuclease-defective CRISPR/Cas9 proteins fused with proteins that effect modifications in DNA chemistry resulting in cytosine methylation or in histone post-translational modification such as histone methylation or de-methylation are used.

Any method of DNA targeting known in the art can be used to substitute for CRISPR/Cas9 in order to effect disruption of expression of a target gene (such as SRC-3). Such methods include DNA-targeting molecule that targets the gene, such as one or more zinc finger proteins (ZFP) or transcription activator-like proteins (TAL), fused to an effector protein such as an endonuclease. Examples include ZFNs, TALEs, and TALENs.

In some embodiments, the DNA-targeting molecule comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion. Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice.

In some embodiments, the DNA-targeting molecule comprises a zinc-finger DNA binding domain fused to a DNA cleavage domain to form a zinc-finger nuclease (ZFN). In some embodiments, fusion proteins comprise the cleavage domain (or cleavage half-domain) from at least one Type liS restriction enzyme and one or more zinc finger binding domains, which may or may not be engineered. In some embodiments, the cleavage domain is from the Type liS restriction endonuclease Fok I. Fok I generally catalyzes double-stranded cleavage of DNA, at 9 nucleotides from its recognition site on one strand and 13 nucleotides from its recognition site on the other.

Many gene-specific engineered zinc fingers are available commercially. For example, Sangamo Biosciences (Richmond, CA, USA) has developed a platform (CompoZr) for zinc-finger construction in partnership with Sigma-Aldrich (St. Louis, MO, USA), allowing investigators to bypass zinc-finger construction and validation altogether, and provides specifically targeted zinc fingers for thousands of proteins (Gaj et al., Trends in Biotechnology, 2013, 31 (7), 397-405). In some embodiments, commercially available zinc fingers are used or are custom designed. (See, for example, Sigma-Aldrich catalog numbers CSTZEND, CSTZFN, CTil-lKT, and PZD0020).

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 2011/0301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NO binds to T and non-canonical (atypical) RVDs are also known. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE nuclease (TALEN). In some aspects the TALEN is a fusion protein comprising a DNA-binding domain derived from a TALE and a nuclease catalytic domain to cleave a nucleic acid target sequence.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., 2013). A library of TALENs targeting 18,740 human protein-coding genes has been constructed (Kim et al., 2013). Custom-designed TALE arrays are commercially available through Cellectis Bioresearch (Paris, France), Transposagen Biopharmaceuticals (Lexington, KY, USA), and Life Technologies (Grand Island, NY, USA). Specifically, TALENs that target CD38 are commercially available (See Gencopoeia, catalog numbers HTN222870-1, HTN222870-2, and HTN222870-3). Exemplary molecules are described, e.g., in U.S. Patent Publication Nos. US 2014/0120622, and 2013/0315884.

In some embodiments the TALENs are introduced as trans genes encoded by one or more plasmid vectors. In some aspects, the plasmid vector can contain a selection marker which provides for identification and/or selection of cells which received said vector.

In some embodiments, the alteration of the gene of interest is carried out using one or more DNA-binding nucleic acids, such as alteration via an RNA-guided endonuclease (RGEN). For example, the alteration can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into a cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. As used herein, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

In certain embodiments, the CRISPR system induces double stranded breaks (DSBs) at a target site, including at a target sequence on the desired gene (such as SRC-3), followed by disruptions or alterations as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

In some embodiments, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2.

In some embodiments, the CRISPR enzyme is Cas9 (e.g., from *S. pyogenes* or *S. pneumonia*). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme and the scFv antibody is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (RNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme itself and the larger CRISPR/Cas9/targeting antibody/gene targeting small guide RNA (sgRNA) fusion protein may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US20110059502, incorporated herein by reference.

V. Complexes

Certain embodiments herein concern fusion proteins complexed with ribonucleotides forming a fusion protein ribonucleotides complex. The ribonucleotides may be an sgRNA that interacts with the fusion protein, or domains thereof, to affect a target gene (such as SRC-3). The target gene may be any gene. In some embodiments, the target gene is an oncogene, a tumor suppressor gene, a mutated gene, an immunostimulatory gene, an immunomodulatory gene, or a gene associated with a disease.

The fusion protein may comprise at least one scFV. The scFv may target any surface antigen, such as any tumor associated antigen. In some embodiments, the surface antigen comprises an immune cell marker, an estrogen receptor, a tyrosine kinase receptor, a growth factor receptor, or an immune checkpoint receptor. The scFv may comprise all or a portion of a therapeutic antibody including, but not limited to, 3F8, Abagovomab, Abciximab, Abituzumab, Abrezekimab, Abrilumab, Actoxumab, Adalimumab, Adecatumumab, Aducanumab, Afasevikumab, Afelimomab, Alacizumab pegol, Alemtuzumab, Alirocumab, Altumomab pentetate, Amatuximab, Amivantamab, Anatumomab mafenatox, Andecaliximab, Anetumab ravtansine, Anifrolumab, Ansuvimab, Anrukinzumab, Apolizumab, Aprutumab ixadotin, Arcitumomab, Ascrinvacumab, Aselizumab, Atezolizumab, Atidortoxumab, Atinumab, Atoltivimab, Atoltivimab/maftivimab/odesivimab, Atorolimumab, Avelumab, Azintuxizumab vedotin, Bamlanivimab, Bapineuzumab, Basiliximab, Bavituximab, BCD-100, Bebtelovimab, Bectumomab, Begelomab, Belantamab mafodotin, Belimumab, Bemarituzumab, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab, Bleselumab, Blinatumomab, Blontuvetmab, Blosozumab, Bococizumab, Brazikumab, Brentuximab vedotin, anaplastic large-cell lymphoma, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Casirivimab, Capromab, Carlumab, Carotuximab, Catumaxomab, CBR96-doxorubicin immunoconjugate, Cedelizumab, Cemiplimab, Cergutuzumab amunaleukin, Certolizumab pegol, Cetrelimab, Cetuximab, Cibisatamab, Cilgavimab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, Crizanlizumab, Crotedumab, CR6261, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Dinutuximab beta, Diridavumab, Domagrozumab, Dorlimomab aritox, Dostarlimab, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epcoritamab, Epitumomab cituxetan, Epratuzumab, Eptinezumab, Erenumab, Erlizumab, Ertumaxomab, Etaracizumab, Etesevimab, Etigilimab, Etrolizumab, Evinacumab, Evolocumab, Exbivirumab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotamab, Ganitumab, Gantenerumab, Gatipotuzumab, Gavilimomab, Gedivumab, ozogamicin, Gemtuzumab Gevokizumab, Gilvetmab, Gimsilumab, Girentuximab, Glembatumumab vedotin, Golimumab, Gomiliximab, Gosuranemab, Guselkumab, Ianalumab, Ibalizumab, Sintilimab, Ibritumomab tiuxetan, Icrucumab, Idarucizumab, Ifabotuzumab, Igovomab, Iladatuzumab vedotin, Imalumab, Imaprelimab, Imciromab, Imdevimab, Imgatuzumab, Inclacumab, Indatuximab ravtansine, Indusatumab vedotin, Inebilizumab, Infliximab, Intetumumab, Inolimomab, Inotuzumab ozogamicin, Ipilimumab, Iomab-B, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Loncastuximab tesirine, Losatuxizumab vedotin, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lupartumab, Lupartumab amadotin, Lutikizumab, Maftivimab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odesivimab, Odulimomab, Ofatumumab, multiple sclerosis, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Prezalumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Regdanvimab, Relatlimab, Remtolumab, Reslizumab, Rilotumumab, Rinucumab, Risankizumab, Rituximab, Rivabazumab pegol, Robatumumab, Rmab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab pendetide, Secukinumab, Selicrelumab, Seribantumab, Setoxaximab, Setrusumab, Sevirumab, Sibrotuzumab, SGN-CD19A, SHP647, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Sotrovimab, Spartalizumab, Spesolimab, Stamulumab, Sulesomab, Suptavumab, Sutimlimab, Suvizumab, Suvratoxumab, Tabalumab, Tacatuzumab tetraxetan, Tadocizumab, Tafasitamab, Talacotuzumab, Talizumab, Talquetamab, Tamtuvetmab, Tanezumab, Taplitumomab paptox, Tarextumab, Tavolimab, Teclistamab, Tefibazumab, Telimomab aritox, Telisotuzumab, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tildrakizumab, Tigatuzumab, Timigutuzumab, Timolumab, tiragolumab, Tiragotumab, Tislelizumab, Tisotumab vedotin, Tixagevimab, TNX-650, Tocilizumab, Tomuzotuximab, Toralizumab, Tosatoxumab, Tositumomab, Tovetumab, Tralokinumab, Trastuzumab, Trastuzumab duocarmazine, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab, or Zolimomab aritox.

In some embodiments, the surface antigen comprises CD319/CS1, ROR1, CD20, carcinoembryonic antigen, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, WT-1, EGFRvIII, TRAIL/DR4, VEGFR2, fibroblast growth factor receptors (FGFR1, FGFR2, FGFR3, FGFR4), E-cadherin, collagen-binding integrins (α1β1, α2β1, α10β1, α11β1), leukocyte-binding integrins (e.g., αLB2, αMβ2, α4β1), TGFBR, 4-1BB (CD137), 5'-nucleotidase, 5T4, activated F9, F10, activin receptor-like kinase 1, ACVR2B, adenocarcinoma antigen, alpha-fetoprotein, Alpha-synuclein, amyloid, angiopoietin 2, angiopoietin 3, anthrax toxin, protective antigen, AOC3, AOC3 (VAP-1), AXL, *Bacillus anthracis* anthrax, BAFF-R, B-cell activating factor (BAFF), B-cell maturation antigen (BCMA), CD3, B-lymphoma cell, C242 antigen, C5, CA-125, CA-125 (imitation), calcitonin, calcitonin gene-related peptide, calcitonin gene-related peptide alpha and beta, calcitonin gene-related peptide receptor (CGRP), CanAg (a glycoform of MUC1), *Canis lupus familiaris* IL31, carbonic anhydrase 9 (CA-IX), Carcinoembryonic antigen (CEA), Carcinoembryonic antigen (CEA)-related antigen, cardiac myosin, CCL11 (eotaxin-1), CCR2, CCR4, CCR5, CD11, CD18, CD123, CD125, CD134, CD147 (basigin), CD4, CD15, CD152, CD154 (CD40L), CD19, CD3E, CD2, CD20, CD200, CD22, CD23 (IgE receptor), CD25 (a chain of IL-2 receptor), CD27, CD276, CD278, aka ICOS, CD28, CD3, CD3, CD20, CD30 (TNFRSF8), CD319, CD33, CD37, CD38, CD3E, CD3E, MS4A1, CD20, CD40, CD41 (integrin alpha-IIb), CD44 v6, CD45, CD5, CD51, CD52, CD56, CD6, CD70, CD74, CD79B, CD80, CEACAM5, Claudin 18 Isoform 2, *Clostridium difficile*, clumping factor A, c-Met, coagulation factor III, complement C5a, complement component 1s (C1s), Complement factor D (CFD), connective tissue growth factor (CTGF), CSF1, macrophage colony stimulating factor (MCSF), CSFIR, CSF2, CTLA-4, CXCL10 (IP-10), CXCR4 (CD184), cytomegaIovirus, cytomegaIovirus glycoprotein B, dabigatran, dendritic cell-associated lectin 2, DLL3, DLL4, DLL4 and VEGFA, DPP4, DR5, *E. coli* shiga toxin type-1, *E. coli* shiga toxin type-2, Ebola virus glycoprotein, EGFL7, EGFR, EGFR extracellular domain III, endoglin, endotoxin, EpCAM, EpCAM, CD3, EPHA3, ephrin receptor A3, Epidermal growth factor receptor (EGFR), Epidermal growth factor receptor (EGFR), cMet, Epidermal growth factor receptor (EGFR), HER1, epidermal growth receptor factor (EGRF), ERBB1 HER1, episialin, ERBB3 (HER3), *Escherichia coli*, F protein of respiratory syncytial virus, FAP (gene) (FAP), FCGRT, FGF 23, FGFR2, fibrin II, beta chain, fibronectin extra domain-B, folate hydrolase, folate receptor 1, folate receptor alpha, Frizzled receptor, GD2 ganglioside, GDF-8, gelatinase B, glucagon receptor (GCGR), Glutamate carboxypeptidase II, glypican 3, GMCSF, GMCSF receptor α-chain, GPNMB, GPRC5D, CD3, growth differentiation factor 8, GUCY2C, Hemagglutinin (influenza), hepatitis B surface antigen, hepatitis B virus, Hepatocyte growth factor (HGF), HER1, HER2, HER2/neu, HER2/neu, CD3, HGFR, histone complex, HIV-1, HLA-DR, Hsp90, human scatter factor receptor kinase, ICAM-1, ICAM-1 (CD54), IFN receptor, IFN-gamma, IFN-alpha/beta receptor, IFN-α, IgE, IgE Fc region, IGF-1 receptor (CD221), IGF-1, IGF-2, IGF-2, IGHE, IL-1, IL-12, IL-23, IL-13, IL-17, IL-17A, IL-17A, IL-17F, IL-17A, IL-17F, IL-17AF, IL-17A, TNF, IL-1a, IL-1beta, IL-2, IL-20, IL-22, IL-23, IL-23A, IL-3 receptor, IL-31 receptor A, IL-4, IL-4Ra, IL-5, IL-6, IL-6 receptor, IL-9, inducible T-cell co-stimulatory ligand (ICOSL), integrin α4, integrin α4 beta7, integrin α5beta1, integrin αIIbβ3, integrin avbeta3, integrin beta7, Interleukin 36 receptor (IL1RL2/IL1RAP), ITGA2 (CD49b), ITGB2 (CD18), kallikrein, KIR2D, LAG3, Lewis-Y antigen, LFA-1 (CD11a), LINGO-1, lipoteichoic acid, LIV-1, LOXL2, LRRC15, L-selectin (CD62L), lymphotoxin alpha (LTA), LYPD3, macrophage migration inhibitory factor (MIF), MASP-2, MCP-1, melanoma cell adhesion molecule (MCAM), mesothelin, mesothelin (MSLN), MS4A1, MST1R (aka RON), MUC1, MUC5AC, mucosal addressin cell adhesion molecule, myelin-associated glycoprotein, myostatin, NCA-90 (granulocyte antigen), nectin-4, nerve growth factor (NGF), nerve growth factor (NGF), NGF, NGNA ganglioside, NKG2A, NOGO-A, Notch 1, Notch receptor, NRP1, OX-40, OxLDL, PCDCl, PCDCl, CD279, PCDP1, PCSK9, PD-1, PDGFRA, PDGFRB, PD-L1, phosphate-sodium co-transporter, phosphatidylserine, *Pseudomonas aeruginosa, Pseudomonas aeruginosa* type III secretion system, PTK7, rabies virus G glycoprotein, rabies virus glycoprotein, RANKL, repulsive guidance molecule A (RGMA), respiratory syncytial virus, RHD (gene) (RHD), Rhesus factor, root plate-specific spondin 3, ROR1, RSV fusion glycoprotein, RSVFR, RTN4, sclerostin, sclerostin (SOST), SDC1, selectin P, serum amyloid A protein, serum amyloid P component, SLAMF7, SLITRK6, SOST, sphingosine-1-phosphate, spike protein receptor binding domain (RBD) of SARS-COV-2, *Staphylococcus aureus, Staphylococcus aureus* alpha toxin, *Staphylococcus aureus* bi-component leukocidin, STEAP1, TAG-72, tau protein, T-cell receptor, TEM1, tenascin C, TGF-beta, TGF-beta1, TGF-beta2, thymic stromal lymphopoietin (TSLP), TIGIT, tissue factor pathway inhibitor (TFPI), TNF, TNF-α, TRAIL-R1, TRAIL-R2, TROP-2, tumor antigen CTAA16.88, tumor necrosis factor receptor (TNFR) superfamily member 4, tumor necrosis factor related activation protein (TRAP), tumor specific glycosylation of MUC1, Tumor-associated glycoprotein 72 (TAG-72), TWEAK receptor, TYRP1 (glycoprotein 75), vascular endothelial growth factor A (VEGFA), VEGF-A, VEGF-A and Ang-2, VEGFR-1, VEGFR2, vimentin, VISTA (protein) (VSIR), VWF, Zaire ebolavirus glycoprotein, beta-amyloid, or beta-amyloid (1-40 and 1-42).

The antibody may target any antigen, including at least TGFBR, 4-1BB (CD137), 5'-nucleotidase, 5T4, activated F9, F10, activin receptor-like kinase 1, ACVR2B, adenocarcinoma antigen, alpha-fetoprotein, Alpha-synuclein, amyloid, angiopoietin 2, angiopoietin 3, anthrax toxin, protective antigen, AOC3, AOC3 (VAP-1), AXL, *Bacillus anthracis* anthrax, BAFF—R, B-cell activating factor (BAFF), B-cell maturation antigen (BCMA), CD3, B-lymphoma cell, C242 antigen, C5, CA-125, CA-125 (imitation), calcitonin, calcitonin gene-related peptide, calcitonin gene-related peptide alpha and beta, calcitonin gene-related peptide receptor (CGRP), CanAg (a glycoform of MUC1), *Canis lupus familiaris* IL31, carbonic anhydrase 9 (CA-IX), Carcinoembryonic antigen (CEA), Carcinoembryonic antigen (CEA)-related antigen, cardiac myosin, CCL11 (eotaxin-1), CCR2, CCR4, CCR5, CD11, CD18, CD123, CD125, CD134, CD147 (basigin), CD4, CD15, CD152, CD154 (CD40L), CD19, CD3E, CD2, CD20, CD200, CD22, CD23 (IgE receptor), CD25 (a chain of IL-2 receptor), CD27, CD276, CD278, aka ICOS, CD28, CD3, CD3, CD20, CD30 (TNFRSF8), CD319, CD33, CD37, CD38, CD3E, CD3E, MS4A1, CD20, CD40, CD41 (integrin alpha-IIb), CD44 v6, CD45, CD5, CD51, CD52, CD56, CD6, CD70, CD74, CD79B, CD80, CEACAM5, Claudin 18 Isoform 2, *Clostridium difficile*, clumping factor A, c-Met, coagulation factor III, complement C5a, complement component 1s (C1s), Complement factor D (CFD), connective tissue growth factor (CTGF), CSF1, macrophage colony stimulating factor (MCSF), CSFIR, CSF2, CTLA-4, CXCL10 (IP-10), CXCR4 (CD184), cytomegaIovirus, cytomegaIovirus glycoprotein B, dabigatran, dendritic cell-associated lectin 2, DLL3, DLL4, DLL4 and VEGFA, DPP4, DR5, *E. coli* shiga toxin type-1, *E. coli* shiga toxin type-2, Ebola virus glycoprotein, EGFL7, EGFR, EGFR extracellular domain III, endoglin, endotoxin, EpCAM, EpCAM, CD3, EPHA3, ephrin receptor A3, Epidermal growth factor receptor (EGFR), Epidermal growth factor receptor (EGFR), cMet, Epidermal growth factor receptor (EGFR), HER1, epidermal growth receptor factor (EGRF), ERBB1 HER1, episialin, ERBB3 (HER3), *Escherichia coli*, F protein of respiratory syncytial virus, FAP (gene) (FAP), FCGRT, FGF 23, FGFR2, fibrin II, beta chain, fibronectin extra domain-B, folate hydrolase, folate receptor 1, folate receptor alpha, Frizzled receptor, GD2 ganglioside, GDF-8, gelatinase B, glucagon receptor (GCGR), Glutamate carboxypeptidase II, glypican 3, GMCSF, GMCSF receptor α-chain, GPNMB, GPRC5D, CD3, growth differentiation factor 8, GUCY2C, Hemagglutinin (influenza), hepatitis B surface antigen, hepatitis B virus, Hepatocyte growth factor (HGF), HER1, HER2, HER2/neu, HER2/neu, CD3, HGFR, histone complex, HIV-1, HLA-DR, Hsp90, human scatter factor receptor kinase, ICAM-1, ICAM-1 (CD54), IFN receptor, IFN-gamma, IFN-alpha/beta receptor, IFN-α, IgE, IgE Fc region, IGF-1 receptor (CD221), IGF-1, IGF-2, IGF-2, IGHE, IL-1, IL-12, IL-23, IL-13, IL-17, IL-17A, IL-17A, IL-17F, IL-17A, IL-17F, IL-17AF, IL-17A, TNF, IL-1a, IL-1beta, IL-2, IL-20, IL-22, IL-23, IL-23A, IL-3 receptor, IL-31 receptor A, IL-4, IL-4Ra, IL-5, IL-6, IL-6 receptor, IL-9, inducible T-cell co-stimulatory ligand (ICOSL), integrin α4, integrin α4 beta7, integrin α5beta1, integrin αIIbβ3, integrin avbeta3, integrin beta7, Interleukin 36 receptor (IL1RL2/IL1RAP), ITGA2 (CD49b), ITGB2 (CD18), kallikrein, KIR2D, LAG3, Lewis-Y antigen, LFA-1 (CD11a), LINGO-1, lipoteichoic acid, LIV-1, LOXL2, LRRC15, L-selectin (CD62L), lymphotoxin alpha (LTA), LYPD3, macrophage migration inhibitory factor (MIF), MASP-2, MCP-1, melanoma cell adhesion molecule (MCAM), mesothelin, mesothelin (MSLN), MS4A1, MSTIR (aka RON), MUC1, MUC5AC, mucosal addressin cell adhesion molecule, myelin-associated glycoprotein, myostatin, NCA-90 (granulocyte antigen), nectin-4, nerve growth factor (NGF), nerve growth factor (NGF), NGF, NGNA ganglioside, NKG2A, NOGO-A, Notch 1, Notch receptor, NRP1, OX-40, oxLDL, PCDCl, PCDCl, CD279, PCDP1, PCSK9, PD-1, PDGFRA, PDGFRB, PD-L1, phosphate-sodium co-transporter, phosphatidylserine, *Pseudomonas aeruginosa, Pseudomonas aeruginosa* type III secretion system, PTK7, rabies virus G glycoprotein, rabies virus glycoprotein, RANKL, repulsive guidance molecule A (RGMA), respiratory syncytial virus, RHD (gene) (RHD), Rhesus factor, root plate-specific spondin 3, ROR1, RSV fusion glycoprotein, RSVFR, RTN4, sclerostin, sclerostin (SOST), SDC1, selectin P, serum amyloid A protein, serum amyloid P component, SLAMF7, SLITRK6, SOST, sphingosine-1-phosphate, spike protein receptor binding domain (RBD) of SARS-COV-2, *Staphylococcus aureus, Staphylococcus aureus* alpha toxin, *Staphylococcus aureus* bi-component leukocidin, STEAP1, TAG-72, tau protein, T-cell receptor, TEM1, tenascin C, TGF-beta, TGF-beta1, TGF-beta2, thymic stromal lymphopoietin (TSLP), TIGIT, tissue factor pathway inhibitor (TFPI), TNF, TNF-α, TRAIL-R1, TRAIL-R2, TROP-2, tumor antigen CTAA16.88, tumor necrosis factor receptor (TNFR) superfamily member 4, tumor necrosis factor related activation protein (TRAP), tumor specific glycosylation of MUC1, Tumor-associated glycoprotein 72 (TAG-72), TWEAK receptor, TYRP1 (glycoprotein 75), vascular endothelial growth factor A (VEGFA), VEGF-A, VEGF-A and Ang-2, VEGFR-1, VEGFR2, vimentin, VISTA (protein) (VSIR), VWF, Zaire ebolavirus glycoprotein, beta-amyloid, or beta-amyloid (1-40 and 1-42).

A. Proteins

Where a protein is specifically mentioned herein, it is in general a reference to a native (wild-type) or recombinant (modified) protein or, optionally, a protein in which any signal sequence has been removed. The protein may be isolated directly from the organism of which it is native, produced by recombinant DNA/exogenous expression methods, or produced by solid-phase peptide synthesis (SPPS) or other in vitro methods. In particular embodiments, there are isolated nucleic acid segments and recombinant vectors incorporating nucleic acid sequences that encode a polypeptide (e.g., an antibody or fragment thereof). The term "recombinant" may be used in conjunction with a polypeptide or the name of a specific polypeptide, and this generally refers to a polypeptide produced from a nucleic acid molecule that has been manipulated in vitro or that is a replication product of such a molecule.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino acid residues or greater, and any range derivable therein, or derivative of a corresponding amino sequence described or referenced herein. It is contemplated that polypeptides may be mutated by truncation, rendering them shorter than their corresponding wild-type form, also, they might be altered by fusing or conjugating a heterologous protein or polypeptide sequence with a particular function (e.g., for targeting or localization, for enhanced immunogenicity, for purification purposes, etc.). As used herein, the term "domain" refers to any distinct functional or structural unit of a protein or polypeptide, and generally refers to a sequence of amino acids with a structure or function recognizable by one skilled in the art.

The polypeptides, proteins, or polynucleotides encoding such polypeptides or proteins of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (or any derivable range therein) or more variant amino acids or nucleic acid substitutions or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000, 1500 or more contiguous amino acids or nucleic acids, or any range derivable therein, of SEQ ID NOs 1-10.

SEQ ID NO. 1: Amino acid sequence for 6xHis purification tag (6His)
HHHHHH

SEQ ID NO. 2: Amino acid sequence for Cell Penetrating Peptide (CPP)
KLALKLALKALKAALK SEQ ID NO. 3: Amino acid sequence for Linker 1
G SEQ ID NO. 4: Amino acid sequence for Linker 2
LFPTI SEQ ID NO. 5: Amino acid sequence for CRISPR/Cas9 nuclease
DKKYSIGLDIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRTF

-continued

DNGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVY

NELTKVKYVTEGMRKPAFLSGEQKKAIVDLLFKTNRKVTVKQLKEDYFKKIECFDS

VEISGVEDRFNASLGTYHDLLKIIKDKDFLDNEENEDILEDIVLTLTLFEDREMIEERL

KTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD

SEQ ID NO. 6: Amino acid sequence for Linker 3
GPG

SEQ ID NO. 7: Amino acid sequence for TEV protease
ENLYFQG

SEQ ID NO. 8: Amino acid sequence for Linker 4
AG

SEQ ID NO. 9: Amino acid sequence for FLAG-tag
DYKDDDDKG

SEQ ID NO. 10: Amino acid sequence for CD25 scFv
QVQLVQSGAEVKKPGSSVKVSCKASGYTFTSYRMHWVRQAPGQGLEWIGYINPSTG

YTEYNQKFKDKATITADESTNTAYMELSSLRSEDTAVYYCARGGGVFDYWGQGTL

VTVSSGGGGSGGGGSGGGGSDIQMTQSPSTLSASVGDRVITITCSASSSISYMHWYQ

QKPGKAPKLLIYTTSNLASGVPARFSGSGSGTEFTLTISSLQPDDFATYYCHQRSTYPL

TFGQGTKVEVKR

SEQ ID NO. 11: Amino acid sequence for CRISPR/Cas9 nuclease
DKKYSIGLDIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDL

NPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADL

FLAAKNLSDAILLSDILRVNTEITKAPLSASMIKRYDEHHQDLTLLKALVRQQLPEKY

KEIFFDQSKNGYAGYIDGGASQEEFYKFIKPILEKMDGTEELLVKLNREDLLRKQRTF

DNGSIPHQIHLGELHAILRRQEDFYPFLKDNREKIEKILTFRIPYYVGPLARGNSRFAW

MTRKSEETITPWNFEEVVDKGASAQSFIERMTNFDKNLPNEKVLPKHSLLYEYFTVY

NELTKVKYVTEGMRKPAFLSGEQKKAIVDLLFKTNRKVTVKQLKEDYFKKIECFDS

VEISGVEDRFNASLGTYHDLLKIIKDKDFLDNEENEDILEDIVLTLTLFEDREMIEERL

-continued

```
KTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD
```

The nucleotide as well as the protein, polypeptide, and peptide sequences for various genes have been previously disclosed, and may be found in the recognized computerized databases. Two commonly used databases are the National Center for Biotechnology Information's GenBank® and GenPept® databases (on the World Wide Web at ncbi.nlm-.nih.gov/) and The Universal Protein Resource (UniProt; on the World Wide Web at uniprot.org). The coding regions for these genes may be amplified and/or expressed using the techniques disclosed herein or as would be known to those of ordinary skill in the art.

It is contemplated that in compositions of the disclosure, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein).

1. Variant Polypeptides

The following is a discussion of changing the amino acid subunits of a protein to create an equivalent, or even improved, second-generation variant polypeptide or peptide. For example, certain amino acids may be substituted for other amino acids in a protein or polypeptide sequence with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence and in its corresponding DNA coding sequence, and nevertheless produce a protein with similar or desirable properties. It is thus contemplated by the inventors that various changes may be made in the DNA sequences of genes which encode proteins without appreciable loss of their biological utility or activity.

Amino acid sequence variants of the disclosure can be substitutional, insertional, or deletion variants. A variation in a polypeptide of the disclosure may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the protein or polypeptide, as compared to wild-type. A variant can comprise an amino acid sequence that is at least 50%, 60%, 70%, 80%, or 90%, including all values and ranges there between, identical to any sequence provided or referenced herein. A variant can include 2, 3, 4, 5, 6, 7, 8, 9, 10, 11, 12, 13, 14, 15, 16, 17, 18, 19, 20, or more substitute amino acids.

It also will be understood that amino acid and nucleic acid sequences may include additional residues, such as additional N- or C-terminal amino acids, or 5' or 3' sequences, respectively, and yet still be essentially identical as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

Deletion variants typically lack one or more residues of the native or wild type protein. Individual residues can be deleted or a number of contiguous amino acids can be deleted. A stop codon may be introduced (by substitution or insertion) into an encoding nucleic acid sequence to generate a truncated protein.

Insertional mutants typically involve the addition of amino acid residues at a non-terminal point in the polypeptide. This may include the insertion of one or more amino acid residues. Terminal additions may also be generated and can include fusion proteins which are multimers or concatemers of one or more peptides or polypeptides described or referenced herein.

Substitutional variants typically contain the exchange of one amino acid for another at one or more sites within the protein or polypeptide, and may be designed to modulate one or more properties of the polypeptide, with or without the loss of other functions or properties. Substitutions may be conservative, that is, one amino acid is replaced with one of similar chemical properties. "Conservative amino acid substitutions" may involve exchange of a member of one amino acid class with another member of the same class. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Conservative amino acid substitutions may encompass non-naturally occurring amino acid residues, which are typically incorporated by chemical peptide synthesis rather than by synthesis in biological systems. These include peptidomimetics or other reversed or inverted forms of amino acid moieties.

Alternatively, substitutions may be "non-conservative", such that a function or activity of the polypeptide is affected. Non-conservative changes typically involve substituting an amino acid residue with one that is chemically dissimilar, such as a polar or charged amino acid for a nonpolar or uncharged amino acid, and vice versa. Non-conservative substitutions may involve the exchange of a member of one of the amino acid classes for a member from another class.

2. Considerations for Substitutions

One skilled in the art can determine suitable variants of polypeptides as set forth herein using well-known techniques. One skilled in the art may identify suitable areas of the molecule that may be changed without destroying activity by targeting regions not believed to be important for activity. The skilled artisan will also be able to identify amino acid residues and portions of the molecules that are conserved among similar proteins or polypeptides. In further embodiments, areas that may be important for biological activity or for structure may be subject to conservative amino acid substitutions without significantly altering the biological activity or without adversely affecting the protein or polypeptide structure.

In making such changes, the hydropathy index of amino acids may be considered. The hydropathy profile of a protein is calculated by assigning each amino acid a numerical value ("hydropathy index") and then repetitively averaging these values along the peptide chain. Each amino acid has been assigned a value based on its hydrophobicity and charge characteristics. They are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5). The importance of the hydropathy amino acid index in conferring interactive biologic function on a protein is generally understood in the art (Kyte et al., J. Mol. Biol. 157:105-131 (1982)). It is accepted that the relative hydropathic character of the amino acid contributes to the secondary structure of the resultant protein or polypeptide, which in turn defines the interaction of the protein or polypeptide with other molecules, for example, enzymes, substrates, receptors, DNA, antibodies, antigens, and others. It is also known that certain amino acids may be substituted for other amino acids having a similar hydropathy index or score, and still retain a similar biological activity. In making changes based upon the hydropathy index, in certain embodiments, the substitution of amino acids whose hydropathy indices are within +2 is included. In some aspects of the present disclosure, those that are within +1 are included, and in other aspects of the present disclosure, those within +0.5 are included.

It also is understood in the art that the substitution of like amino acids can be effectively made based on hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. In certain embodiments, the greatest local average hydrophilicity of a protein, as governed by the hydrophilicity of its adjacent amino acids, correlates with its immunogenicity and antigen binding, that is, as a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, in certain embodiments, the substitution of amino acids whose hydrophilicity values are within ±2 are included, in other embodiments, those which are within ±1 are included, and in still other embodiments, those within ±0.5 are included. In some instances, one may also identify epitopes from primary amino acid sequences based on hydrophilicity. These regions are also referred to as "epitopic core regions." It is understood that an amino acid can be substituted for another having a similar hydrophilicity value and still produce a biologically equivalent and immunologically equivalent protein.

Additionally, one skilled in the art can review structure-function studies identifying residues in similar polypeptides or proteins that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar proteins or polypeptides. In view of such information, one skilled in the art may predict the alignment of amino acid residues of an antibody with respect to its three-dimensional structure. One skilled in the art may choose not to make changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using standard assays for binding and/or activity, thus yielding information gathered from such routine experiments, which may allow one skilled in the art to determine the amino acid positions where further substitutions should be avoided either alone or in combination with other mutations. Various tools available to determine secondary structure can be found on the world wide web at expasy.org/proteomics/protein_structure.

In some embodiments of the disclosure, amino acid substitutions are made that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. For example, single or multiple amino acid substitutions (in certain embodiments, conservative amino acid substitutions) may be made in the naturally occurring sequence. Substitutions can be made in that portion of the antibody that lies outside the domain(s) forming intermolecular contacts. In such embodiments, conservative amino acid substitutions can be used that do not substantially change the structural characteristics of the protein or polypeptide (e.g., one or more replacement amino acids that do not disrupt the secondary structure that characterizes the native antibody).

B. Nucleic Acids

In certain embodiments, nucleic acid sequences can exist in a variety of instances such as: isolated segments and recombinant vectors of incorporated sequences or recombinant polynucleotides encoding one or both chains of an antibody, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing described herein. Nucleic acids that encode the epitope to which certain of the antibodies provided herein are also provided. Nucleic acids encoding fusion proteins that include these peptides are also provided. The nucleic acids can be single-stranded or double-stranded and can comprise RNA and/or DNA nucleotides and artificial variants thereof (e.g., peptide nucleic acids).

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. The nucleic acids can be any length. They can be, for example, 5, 10, 15, 20, 25, 30, 35, 40, 45, 50, 75, 100, 125, 175, 200, 250, 300, 350, 400, 450, 500, 750, 1000, 1500, 3000, 5000 or more nucleotides in length, and/or can comprise one or more additional sequences, for example, regulatory sequences, and/or be a part of a larger nucleic acid, for example, a vector. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

1. Mutation

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues are changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. See, eg., Romain Studer et al., Biochem. J. 449: 581-594 (2013). For example, the mutation can quantitatively or qualitatively change the biological activity. Examples of quantitative changes include increasing, reducing or eliminating the activity. Examples of qualitative changes include altering the antigen specificity of an antibody.

2. Short Guide RNAs

In certain embodiments, compositions, including any fusion protein ribonucleotide complex described herein, comprise at least one short guide RNA (sgRNA). The sgRNA may complex with a nuclease, including any CRISPR protein, at a specific sequence. The sgRNA may target a specific gene, including any gene described herein. In certain embodiments, the sgRNA comprises SEQ ID NO: 24: GTCTCAGCCTCGCGCTATGC.

In some embodiments, the sgRNA comprises an RNA comprising 1, 2, 3, 4, 5, 6, 7, 8, 9, 10, 11, 12, 13, 14, 15, 16, 17, 18, 19, or 20 consecutive nucleotides of SEQ ID NO: 24.

VI. Obtaining Encoded Polypeptide Embodiments

In some aspects, there are nucleic acid molecules encoding fusion protein ribonucleotide complex polypeptides. These may be generated by methods known in the art, e.g., phage display, expressed in any suitable recombinant expression system and allowed to assemble to form the molecules of the complex. Such nucleotides that encode the polypeptides include those elsewhere herein.

```
SEQ ID NO. 12: Nucleotide sequence for 6xHis purification tag (6His)
CACCACCATCATCATCAT

SEQ ID NO. 13: Nucleotide sequence for Cell Penetrating Peptide (CPP)
AAGCTGGCCCTGAAGCTGGCCCTGAAGGCCCTGAAGGCCGCCCTGAAG

SEQ ID NO. 14: Nucleotide sequence for Linker 1
GGC

SEQ ID NO. 15: Nucleotide sequence for Linker 2
CTGTTCCCCACCATC
```

-continued

SEQ ID NO. 16: Nucleotide sequence for CRISPR/Cas9 nuclease
GACAAGAAGTACAGCATCGGCCTGGACATCGGCACCAACAGCGTGGG

CTGGGCCGTGATCACCGACGAGTACAAGGTGCCCAGCAAGAAGTTCAAGGTGCT

GGGCAACACCGACAGGCACAGCATCAAGAAGAACCTGATCGGCGCCCTGCTGTT

CGACAGCGGCGAGACCGCCGAGGCCACCAGGCTGAAGAGGACCGCCAGGAGGA

GGTACACCAGGAGGAAGAACAGGATCTGCTACCTGCAGGAGATCTTCAGCAACG

AGATGGCCAAGGTGGACGACAGCTTCTTCCACAGGCTGGAGGAGAGCTTCCTGG

TGGAGGAGGACAAGAAGCACGAGAGGCACCCCATCTTCGGCAACATCGTGGACG

AGGTGGCCTACCACGAGAAGTACCCCACCATCTACCACCTGAGGAAGAAGCTGG

TGGACAGCACCGACAAGGCCGACCTGAGGCTGATCTACCTGGCCCTGGCCCACA

TGATCAAGTTCAGGGGCCACTTCCTGATCGAGGGCGACCTGAACCCCGACAACA

GCGACGTGGACAAGCTGTTCATCCAGCTGGTGCAGACCTACAACCAGCTGTTCG

AGGAGAACCCCATCAACGCCAGCGGCGTGGACGCCAAGGCCATCCTGAGCGCCA

GGCTGAGCAAGAGCAGGAGGCTGGAGAACCTGATCGCCCAGCTGCCCGGCGAG

AAGAAGAACGGCCTGTTCGGCAACCTGATCGCCCTGAGCCTGGGCCTGACCCCC

AACTTCAAGAGCAACTTCGACCTGGCCGAGGACGCCAAGCTGCAGCTGAGCAAG

GACACCTACGACGACGACCTGGACAACCTGCTGGCCCAGATCGGCGACCAGTAC

GCCGACCTGTTCCTGGCCGCCAAGAACCTGAGCGACGCCATCCTGCTGAGCGAC

ATCCTGAGGGTGAACACCGAGATCACCAAGGCCCCCCTGAGCGCCAGCATGATC

AAGAGGTACGACGAGCACCACCAGGACCTGACCCTGCTGAAGGCCCTGGTGAGG

CAGCAGCTGCCCGAGAAGTACAAGGAGATCTTCTTCGACCAGAGCAAGAACGGC

TACGCCGGCTACATCGACGGCGGCGCCAGCCAGGAGGAGTTCTACAAGTTCATC

AAGCCCATCCTGGAGAAGATGGACGGCACCGAGGAGCTGCTGGTGAAGCTGAAC

AGGGAGGACCTGCTGAGGAAGCAGAGGACCTTCGACAACGGCAGCATCCCCCAC

CAGATCCACCTGGGCGAGCTGCACGCCATCCTGAGGAGGCAGGAGGACTTCTAC

CCCTTCCTGAAGGACAACAGGGAGAAGATCGAGAAGATCCTGACCTTCAGGATC

CCCTACTACGTGGGCCCCCTGGCCAGGGGCAACAGCAGGTTCGCCTGGATGACC

AGGAAGAGCGAGGAGACCATCACCCCCTGGAACTTCGAGGAGGTGGTGGACAA

GGGCGCCAGCGCCCAGAGCTTCATCGAGAGGATGACCAACTTCGACAAGAACCT

GCCCAACGAGAAGGTGCTGCCCAAGCACAGCCTGCTGTACGAGTACTTCACCGT

GTACAACGAGCTGACCAAGGTGAAGTACGTGACCGAGGGCATGAGGAAGCCCG

CCTTCCTGAGCGGCGAGCAGAAGAAGGCCATCGTGGACCTGCTGTTCAAGACCA

ACAGGAAGGTGACCGTGAAGCAGCTGAAGGAGGACTACTTCAAGAAGATCGAG

TGCTTCGACAGCGTGGAGATCAGCGGCGTGGAGGACAGGTTCAACGCCAGCCTG

GGCACCTACCACGACCTGCTGAAGATCATCAAGGACAAGGACTTCCTGGACAAC

GAGGAGAACGAGGACATCCTGGAGGACATCGTGCTGACCCTGACCCTGTTCGAG

GACAGGGAGATGATCGAGGAGAGGCTGAAGACCTACGCCCACCTGTTCGACGAC

AAGGTGATGAAGCAGCTGAAGAGGAGGAGGTACACCGGCTGGGGCAGGCTGAG

CAGGAAGCTGATCAACGGCATCAGGGACAAGCAGAGCGGCAAGACCATCCTGG

ACTTCCTGAAGAGCGACGGCTTCGCCAACAGGAACTTCATGCAGCTGATCCACG

ACGACAGCCTGACCTTCAAGGAGGACATCCAGAAGGCCCAGGTGAGCGGCCAGG

-continued

GCGACAGCCTGCACGAGCACATCGCCAACCTGGCCGGCAGCCCCGCCATCAAGA

AGGGCATCCTGCAGACCGTGAAGGTGGTGGACGAGCTGGTGAAGGTGATGGGCA

GGCACAAGCCCGAGAACATCGTGATCGAGATGGCCAGGGAGAACCAGACCACC

CAGAAGGGCCAGAAGAACAGCAGGGAGAGGATGAAGAGGATCGAGGAGGGCAT

CAAGGAGCTGGGCAGCCAGATCCTGAAGGAGCACCCCGTGGAGAACACCCAGCT

GCAGAACGAGAAGCTGTACCTGTACTACCTGCAGAACGGCAGGGACATGTACGT

GGACCAGGAGCTGGACATCAACAGGCTGAGCGACTACGACGTGGACCACATCGT

GCCCCAGAGCTTCCTGAAGGACGACAGCATCGACAACAAGGTGCTGACCAGGAG

CGACAAGAACAGGGGCAAGAGCGACAACGTGCCCAGCGAGGAGGTGGTGAAGA

AGATGAAGAACTACTGGAGGCAGCTGCTGAACGCCAAGCTGATCACCCAGAGGA

AGTTCGACAACCTGACCAAGGCCGAGAGGGGCGGCCTGAGCGAGCTGGACAAG

GCCGGCTTCATCAAGAGGCAGCTGGTGGAGACCAGGCAGATCACCAAGCACGTG

GCCCAGATCCTGGACAGCAGGATGAACACCAAGTACGACGAGAACGACAAGCT

GATCAGGGAGGTGAAGGTGATCACCCTGAAGAGCAAGCTGGTGAGCGACTTCAG

GAAGGACTTCCAGTTCTACAAGGTGAGGGAGATCAACAACTACCACCACGCCCA

CGACGCCTACCTGAACGCCGTGGTGGGCACCGCCCTGATCAAGAAGTACCCCAA

GCTGGAGAGCGAGTTCGTGTACGGCGACTACAAGGTGTACGACGTGAGGAAGAT

GATCGCCAAGAGCGAGCAGGAGATCGGCAAGGCCACCGCCAAGTACTTCTTCTA

CAGCAACATCATGAACTTCTTCAAGACCGAGATCACCCTGGCCAACGGCGAGAT

CAGGAAGAGGCCCCTGATCGAGACCAACGGCGAGACCGGCGAGATCGTGTGGG

ACAAGGGCAGGGACTTCGCCACCGTGAGGAAGGTGCTGAGCATGCCCCAGGTGA

ACATCGTGAAGAAGACCGAGGTGCAGACCGGCGGCTTCAGCAAGGAGAGCATCC

TGCCCAAGAGGAACAGCGACAAGCTGATCGCCAGGAAGAAGGACTGGGACCCC

AAGAAGTACGGCGGCTTCGACAGCCCCACCGTGGCCTACAGCGTGCTGGTGGTG

GCCAAGGTGGAGAAGGGCAAGAGCAAGAAGCTGAAGAGCGTGAAGGAGCTGCT

GGGCATCACCATCATGGAGAGGAGCAGCTTCGAGAAGAACCCCATCGACTTCCT

GGAGGCCAAGGGCTACAAGGAGGTGAAGAAGGACCTGATCATCAAGCTGCCCA

AGTACAGCCTGTTCGAGCTGGAGAACGGCAGGAAGAGGATGCTGGCCAGCGCCG

GCGAGCTGCAGAAGGGCAACGAGCTGGCCCTGCCCAGCAAGTACGTGAACTTCC

TGTACCTGGCCAGCCACTACGAGAAGCTGAAGGGCAGCCCCGAGGACAACGAGC

AGAAGCAGCTGTTCGTGGAGCAGCACAAGCACTACCTGGACGAGATCATCGAGC

AGATCAGCGAGTTCAGCAAGAGGGTGATCCTGGCCGACGCCAACCTGGACAAGG

TGCTGAGCGCCTACAACAAGCACAGGGACAAGCCCATCAGGGAGCAGGCCGAG

AACATCATCCACCTGTTCACCCTGACCAACCTGGGCGCCCCCGCCGCCTTCAAGT

ACTTCGACACCACCATCGACAGGAAGAGGTACACCAGCACCAAGGAGGTGCTGG

ACGCCACCCTGATCCACCAGAGCATCACCGGCCTGTACGAGACCAGGATCGACC

TGAGCCAGCTGGGCGGCGAC

SEQ ID NO. 17: Nucleotide sequence for Linker 3
GGCCCCGGC

SEQ ID NO. 18: Nucleotide sequence for TEV protease
GAGAACCTGTACTTCCAGGGC

-continued

SEQ ID NO. 19: Nucleotide sequence for Linker 4
GCCGGC

SEQ ID NO. 20: Nucleotide sequence for FLAG-tag
GACTACAAGGACGACGACGACAAGGGCTGA

SEQ ID NO. 21: Nucleotide sequence for CD25 scFv
CAGGTGCAGCTGGTGCAGAGCGGCGCCGAGGTGAAGAAGCCCGGCAGCAGCGT

GAAGGTGAGCTGCAAGGCCAGCGGCTACACCTTCACCAGCTACAGGATGCACTG

GGTGAGGCAGGCCCCCGGCCAGGGCCTGGAGTGGATCGGCTACATCAACCCCAG

CACCGGCTACACCGAGTACAACCAGAAGTTCAAGGACAAGGCCACCATCACCGC

CGACGAGAGCACCAACACCGCCTACATGGAGCTGAGCAGCCTGAGGAGCGAGG

ACACCGCCGTGTACTACTGCGCCAGGGGCGGCGGCGTGTTCGACTACTGGGGCC

AGGGCACCCTGGTGACCGTGAGCAGCGGCGGCGGCGGCAGCGGCGGCGGCGGC

AGCGGCGGCGGCGGCAGCGACATCCAGATGACCCAGAGCCCCAGCACCCTGAGC

GCCAGCGTGGGCGACAGGGTGATCACCATCACCTGCAGCGCCAGCAGCAGCATC

AGCTACATGCACTGGTACCAGCAGAAGCCCGGCAAGGCCCCCAAGCTGCTGATC

TACACCACCAGCAACCTGGCCAGCGGCGTGCCCGCCAGGTTCAGCGGCAGCGGC

AGCGGCACCGAGTTCACCCTGACCATCAGCAGCCTGCAGCCCGACGACTTCGCC

ACCTACTACTGCCACCAGAGGAGCACCTACCCCCTGACCTTCGGCCAGGGCACC

AAGGTGGAGGTGAAGAGG

SEQ ID NO. 22: Nucleotide sequence for CRISPR/Cas9 nuclease
GACAAGAAGTACAGCATCGGCCTGGACATCGGCACCAACAGCGTGGG

CTGGGCCGTGATCACCGACGAGTACAAGGTGCCCAGCAAGAAGTTCAAGGTGCT

GGGCAACACCGACAGGCACAGCATCAAGAAGAACCTGATCGGCGCCCTGCTGTT

CGACAGCGGCGAGACCGCCGAGGCCACCAGGCTGAAGAGGACCGCCAGGAGGA

GGTACACCAGGAGGAAGAACAGGATCTGCTACCTGCAGGAGATCTTCAGCAACG

AGATGGCCAAGGTGGACGACAGCTTCTTCCACAGGCTGGAGGAGAGCTTCCTGG

TGGAGGAGGACAAGAAGCACGAGAGGCACCCCATCTTCGGCAACATCGTGGACG

AGGTGGCCTACCACGAGAAGTACCCCACCATCTACCACCTGAGGAAGAAGCTGG

TGGACAGCACCGACAAGGCCGACCTGAGGCTGATCTACCTGGCCCTGGCCCACA

TGATCAAGTTCAGGGGCCACTTCCTGATCGAGGGCGACCTGAACCCCGACAACA

GCGACGTGGACAAGCTGTTCATCCAGCTGGTGCAGACCTACAACCAGCTGTTCG

AGGAGAACCCCATCAACGCCAGCGGCGTGGACGCCAAGGCCATCCTGAGCGCCA

GGCTGAGCAAGAGCAGGAGGCTGGAGAACCTGATCGCCCAGCTGCCCGGCGAG

AAGAAGAACGGCCTGTTCGGCAACCTGATCGCCCTGAGCCTGGGCCTGACCCCC

AACTTCAAGAGCAACTTCGACCTGGCCGAGGACGCCAAGCTGCAGCTGAGCAAG

GACACCTACGACGACGACCTGGACAACCTGCTGGCCCAGATCGGCGACCAGTAC

GCCGACCTGTTCCTGGCCGCCAAGAACCTGAGCGACGCCATCCTGCTGAGCGAC

ATCCTGAGGGTGAACACCGAGATCACCAAGGCCCCCCTGAGCGCCAGCATGATC

AAGAGGTACGACGAGCACCACCAGGACCTGACCCTGCTGAAGGCCCTGGTGAGG

CAGCAGCTGCCCGAGAAGTACAAGGAGATCTTCTTCGACCAGAGCAAGAACGGC

TACGCCGGCTACATCGACGGCGGCGCCAGCCAGGAGGAGTTCTACAAGTTCATC

AAGCCCATCCTGGAGAAGATGGACGGCACCGAGGAGCTGCTGGTGAAGCTGAAC

AGGGAGGACCTGCTGAGGAAGCAGAGGACCTTCGACAACGGCAGCATCCCCCAC

-continued

CAGATCCACCTGGGCGAGCTGCACGCCATCCTGAGGAGGCAGGAGGACTTCTAC

CCCTTCCTGAAGGACAACAGGGAGAAGATCGAGAAGATCCTGACCTTCAGGATC

CCCTACTACGTGGGCCCCCTGGCCAGGGGCAACAGCAGGTTCGCCTGGATGACC

AGGAAGAGCGAGGAGACCATCACCCCCTGGAACTTCGAGGAGGTGGTGGACAA

GGGCGCCAGCGCCCAGAGCTTCATCGAGAGGATGACCAACTTCGACAAGAACCT

GCCCAACGAGAAGGTGCTGCCCAAGCACAGCCTGCTGTACGAGTACTTCACCGT

GTACAACGAGCTGACCAAGGTGAAGTACGTGACCGAGGGCATGAGGAAGCCCG

CCTTCCTGAGCGGCGAGCAGAAGAAGGCCATCGTGGACCTGCTGTTCAAGACCA

ACAGGAAGGTGACCGTGAAGCAGCTGAAGGAGGACTACTTCAAGAAGATCGAG

TGCTTCGACAGCGTGGAGATCAGCGGCGTGGAGGACAGGTTCAACGCCAGCCTG

GGCACCTACCACGACCTGCTGAAGATCATCAAGGACAAGGACTTCCTGGACAAC

GAGGAGAACGAGGACATCCTGGAGGACATCGTGCTGACCCTGACCCTGTTCGAG

GACAGGGAGATGATCGAGGAGAGGCTGAAGACCTACGCCCACCTGTTCGACGAC

AAGGTGATGAAGCAGCTGAAGAGGAGGAGGTACACCGGCTGGGGCAGGCTGAG

CAGGAAGCTGATCAACGGCATCAGGGACAAGCAGAGCGGCAAGACCATCCTGG

ACTTCCTGAAGAGCGACGGCTTCGCCAACAGGAACTTCATGCAGCTGATCCACG

ACGACAGCCTGACCTTCAAGGAGGACATCCAGAAGGCCCAGGTGAGCGGCCAGG

GCGACAGCCTGCACGAGCACATCGCCAACCTGGCCGGCAGCCCCGCCATCAAGA

AGGGCATCCTGCAGACCGTGAAGGTGGTGGACGAGCTGGTGAAGGTGATGGGCA

GGCACAAGCCCGAGAACATCGTGATCGAGATGGCCAGGGAGAACCAGACCACC

CAGAAGGGCCAGAAGAACAGCAGGGAGAGGATGAAGAGGATCGAGGAGGGCAT

CAAGGAGCTGGGCAGCCAGATCCTGAAGGAGCACCCCGTGGAGAACACCCAGCT

GCAGAACGAGAAGCTGTACCTGTACTACCTGCAGAACGGCAGGGACATGTACGT

GGACCAGGAGCTGGACATCAACAGGCTGAGCGACTACGACGTGGACCACATCGT

GCCCCAGAGCTTCCTGAAGGACGACAGCATCGACAACAAGGTGCTGACCAGGAG

CGACAAGAACAGGGGCAAGAGCGACAACGTGCCCAGCGAGGAGGTGGTGAAGA

AGATGAAGAACTACTGGAGGCAGCTGCTGAACGCCAAGCTGATCACCCAGAGGA

AGTTCGACAACCTGACCAAGGCCGAGAGGGGCGGCCTGAGCGAGCTGGACAAG

GCCGGCTTCATCAAGAGGCAGCTGGTGGAGACCAGGCAGATCACCAAGCACGTG

GCCCAGATCCTGGACAGCAGGATGAACACCAAGTACGACGAGAACGACAAGCT

GATCAGGGAGGTGAAGGTGATCACCCTGAAGAGCAAGCTGGTGAGCGACTTCAG

GAAGGACTTCCAGTTCTACAAGGTGAGGGAGATCAACAACTACCACCACGCCCA

CGACGCCTACCTGAACGCCGTGGTGGGCACCGCCCTGATCAAGAAGTACCCCAA

GCTGGAGAGCGAGTTCGTGTACGGCGACTACAAGGTGTACGACGTGAGGAAGAT

GATCGCCAAGAGCGAGCAGGAGATCGGCAAGGCCACCGCCAAGTACTTCTTCTA

CAGCAACATCATGAACTTCTTCAAGACCGAGATCACCCTGGCCAACGGCGAGAT

CAGGAAGAGGCCCCTGATCGAGACCAACGGCGAGACCGGCGAGATCGTGTGGG

ACAAGGGCAGGGACTTCGCCACCGTGAGGAAGGTGCTGAGCATGCCCCAGGTGA

ACATCGTGAAGAAGACCGAGGTGCAGACCGGCGGCTTCAGCAAGGAGAGCATCC

TGCCCAAGAGGAACAGCGACAAGCTGATCGCCAGGAAGAAGGACTGGGACCCC

-continued

AAGAAGTACGGCGGCTTCGACAGCCCCACCGTGGCCTACAGCGTGCTGGTGGTG

GCCAAGGTGGAGAAGGGCAAGAGCAAGAAGCTGAAGAGCGTGAAGGAGCTGCT

GGGCATCACCATCATGGAGAGGAGCAGCTTCGAGAAGAACCCCATCGACTTCCT

GGAGGCCAAGGGCTACAAGGAGGTGAAGAAGGACCTGATCATCAAGCTGCCCA

AGTACAGCCTGTTCGAGCTGGAGAACGGCAGGAAGAGGATGCTGGCCAGCGCCG

GCGAGCTGCAGAAGGGCAACGAGCTGGCCCTGCCCAGCAAGTACGTGAACTTCC

TGTACCTGGCCAGCCACTACGAGAAGCTGAAGGGCAGCCCCGAGGACAACGAGC

AGAAGCAGCTGTTCGTGGAGCAGCACAAGCACTACCTGGACGAGATCATCGAGC

AGATCAGCGAGTTCAGCAAGAGGGTGATCCTGGCCGACGCCAACCTGGACAAGG

TGCTGAGCGCCTACAACAAGCACAGGGACAAGCCCATCAGGGAGCAGGCCGAG

AACATCATCCACCTGTTCACCCTGACCAACCTGGGCGCCCCCGCCGCCTTCAAGT

ACTTCGACACCACCATCGACAGGAAGAGGTACACCAGCACCAAGGAGGTGCTGG

ACGCCACCCTGATCCACCAGAGCATCACCGGCCTGTACGAGACCAGGATCGACC

TGAGCCAGCTGGGCGGCGAC

SEQ ID NO. 23: Nucleotide sequence for a CD25 scFc-Cas9 fusion protein

ATGCACCACCATCATCATCATAAGCTGGCCCTGAAGCTGGCCCTGAAGGCCCTGA

AGGCCGCCCTGAAGGGCCAGGTGCAGCTGGTGCAGAGCGGCGCCGAGGTGAAG

AAGCCCGGCAGCAGCGTGAAGGTGAGCTGCAAGGCCAGCGGCTACACCTTCACC

AGCTACAGGATGCACTGGGTGAGGCAGGCCCCCGGCCAGGGCCTGGAGTGGATC

GGCTACATCAACCCCAGCACCGGCTACACCGAGTACAACCAGAAGTTCAAGGAC

AAGGCCACCATCACCGCCGACGAGAGCACCAACACCGCCTACATGGAGCTGAGC

AGCCTGAGGAGCGAGGACACCGCCGTGTACTACTGCGCCAGGGGCGGCGGCGTG

TTCGACTACTGGGGCCAGGGCACCCTGGTGACCGTGAGCAGCGGCGGCGGCGGC

AGCGGCGGCGGCGGCAGCGGCGGCGGCGGCAGCGACATCCAGATGACCCAGAG

CCCCAGCACCCTGAGCGCCAGCGTGGGCGACAGGGTGATCACCATCACCTGCAG

CGCCAGCAGCAGCATCAGCTACATGCACTGGTACCAGCAGAAGCCCGGCAAGGC

CCCCAAGCTGCTGATCTACACCACCAGCAACCTGGCCAGCGGCGTGCCCGCCAG

GTTCAGCGGCAGCGGCAGCGGCACCGAGTTCACCCTGACCATCAGCAGCCTGCA

GCCCGACGACTTCGCCACCTACTACTGCCACCAGAGGAGCACCTACCCCCTGACC

TTCGGCCAGGGCACCAAGGTGGAGGTGAAGAGGCTGTTCCCCACCATCGACAAG

AAGTACAGCATCGGCCTGGACATCGGCACCAACAGCGTGGGCTGGGCCGTGATC

ACCGACGAGTACAAGGTGCCCAGCAAGAAGTTCAAGGTGCTGGGCAACACCGAC

AGGCACAGCATCAAGAAGAACCTGATCGGCGCCCTGCTGTTCGACAGCGGCGAG

ACCGCCGAGGCCACCAGGCTGAAGAGGACCGCCAGGAGGAGGTACACCAGGAG

GAAGAACAGGATCTGCTACCTGCAGGAGATCTTCAGCAACGAGATGGCCAAGGT

GGACGACAGCTTCTTCCACAGGCTGGAGGAGAGCTTCCTGGTGGAGGAGGACAA

GAAGCACGAGAGGCACCCCATCTTCGGCAACATCGTGGACGAGGTGGCCTACCA

CGAGAAGTACCCCACCATCTACCACCTGAGGAAGAAGCTGGTGGACAGCACCGA

CAAGGCCGACCTGAGGCTGATCTACCTGGCCCTGGCCCACATGATCAAGTTCAG

GGGCCACTTCCTGATCGAGGGCGACCTGAACCCCGACAACAGCGACGTGGACAA

GCTGTTCATCCAGCTGGTGCAGACCTACAACCAGCTGTTCGAGGAGAACCCCATC

-continued

AACGCCAGCGGCGTGGACGCCAAGGCCATCCTGAGCGCCAGGCTGAGCAAGAGC

AGGAGGCTGGAGAACCTGATCGCCCAGCTGCCCGGCGAGAAGAAGAACGGCCT

GTTCGGCAACCTGATCGCCCTGAGCCTGGGCCTGACCCCCAACTTCAAGAGCAAC

TTCGACCTGGCCGAGGACGCCAAGCTGCAGCTGAGCAAGGACACCTACGACGAC

GACCTGGACAACCTGCTGGCCCAGATCGGCGACCAGTACGCCGACCTGTTCCTG

GCCGCCAAGAACCTGAGCGACGCCATCCTGCTGAGCGACATCCTGAGGGTGAAC

ACCGAGATCACCAAGGCCCCCCTGAGCGCCAGCATGATCAAGAGGTACGACGAG

CACCACCAGGACCTGACCCTGCTGAAGGCCCTGGTGAGGCAGCAGCTGCCCGAG

AAGTACAAGGAGATCTTCTTCGACCAGAGCAAGAACGGCTACGCCGGCTACATC

GACGGCGGCGCCAGCCAGGAGGAGTTCTACAAGTTCATCAAGCCCATCCTGGAG

AAGATGGACGGCACCGAGGAGCTGCTGGTGAAGCTGAACAGGGAGGACCTGCT

GAGGAAGCAGAGGACCTTCGACAACGGCAGCATCCCCCACCAGATCCACCTGGG

CGAGCTGCACGCCATCCTGAGGAGGCAGGAGGACTTCTACCCCTTCCTGAAGGA

CAACAGGGAGAAGATCGAGAAGATCCTGACCTTCAGGATCCCCTACTACGTGGG

CCCCCTGGCCAGGGGCAACAGCAGGTCGCCTGGATGACCAGGAAGAGCGAGGA

GACCATCACCCCCTGGAACTTCGAGGAGGTGGTGGACAAGGGCGCCAGCGCCCA

GAGCTTCATCGAGAGGATGACCAACTTCGACAAGAACCTGCCCAACGAGAAGGT

GCTGCCCAAGCACAGCCTGCTGTACGAGTACTTCACCGTGTACAACGAGCTGACC

AAGGTGAAGTACGTGACCGAGGGCATGAGGAAGCCCGCCTTCCTGAGCGGCGAG

CAGAAGAAGGCCATCGTGGACCTGCTGTTCAAGACCAACAGGAAGGTGACCGTG

AAGCAGCTGAAGGAGGACTACTTCAAGAAGATCGAGTGCTTCGACAGCGTGGAG

ATCAGCGGCGTGGAGGACAGGTTCAACGCCAGCCTGGGCACCTACCACGACCTG

CTGAAGATCATCAAGGACAAGGACTTCCTGGACAACGAGGAGAACGAGGACATC

CTGGAGGACATCGTGCTGACCCTGACCCTGTTCGAGGACAGGGAGATGATCGAG

GAGAGGCTGAAGACCTACGCCCACCTGTTCGACGACAAGGTGATGAAGCAGCTG

AAGAGGAGGAGGTACACCGGCTGGGGCAGGCTGAGCAGGAAGCTGATCAACGG

CATCAGGGACAAGCAGAGCGGCAAGACCATCCTGGACTTCCTGAAGAGCGACGG

CTTCGCCAACAGGAACTTCATGCAGCTGATCCACGACGACAGCCTGACCTTCAAG

GAGGACATCCAGAAGGCCCAGGTGAGCGGCCAGGGCGACAGCCTGCACGAGCA

CATCGCCAACCTGGCCGGCAGCCCCGCCATCAAGAAGGGCATCCTGCAGACCGT

GAAGGTGGTGGACGAGCTGGTGAAGGTGATGGGCAGGCACAAGCCCGAGAACA

TCGTGATCGAGATGGCCAGGGAGAACCAGACCACCCAGAAGGGCCAGAAGAAC

AGCAGGGAGAGGATGAAGAGGATCGAGGAGGGCATCAAGGAGCTGGGCAGCCA

GATCCTGAAGGAGCACCCCGTGGAGAACACCCAGCTGCAGAACGAGAAGCTGTA

CCTGTACTACCTGCAGAACGGCAGGGACATGTACGTGGACCAGGAGCTGGACAT

CAACAGGCTGAGCGACTACGACGTGGACCACATCGTGCCCCAGAGCTTCCTGAA

GGACGACAGCATCGACAACAAGGTGCTGACCAGGAGCGACAAGAACAGGGGCA

AGAGCGACAACGTGCCCAGCGAGGAGGTGGTGAAGAAGATGAAGAACTACTGG

AGGCAGCTGCTGAACGCCAAGCTGATCACCCAGAGGAAGTTCGACAACCTGACC

AAGGCCGAGAGGGGCGGCCTGAGCGAGCTGGACAAGGCCGGCTTCATCAAGAG

GCAGCTGGTGGAGACCAGGCAGATCACCAAGCACGTGGCCCAGATCCTGGACAG

-continued

```
CAGGATGAACACCAAGTACGACGAGAACGACAAGCTGATCAGGGAGGTGAAGG

TGATCACCCTGAAGAGCAAGCTGGTGAGCGACTTCAGGAAGGACTTCCAGTTCT

ACAAGGTGAGGGAGATCAACAACTACCACCACGCCCACGACGCCTACCTGAACG

CCGTGGTGGGCACCGCCCTGATCAAGAAGTACCCCAAGCTGGAGAGCGAGTTCG

TGTACGGCGACTACAAGGTGTACGACGTGAGGAAGATGATCGCCAAGAGCGAGC

AGGAGATCGGCAAGGCCACCGCCAAGTACTTCTTCTACAGCAACATCATGAACT

TCTTCAAGACCGAGATCACCCTGGCCAACGGCGAGATCAGGAAGAGGCCCCTGA

TCGAGACCAACGGCGAGACCGGCGAGATCGTGTGGGACAAGGGCAGGGACTTC

GCCACCGTGAGGAAGGTGCTGAGCATGCCCCAGGTGAACATCGTGAAGAAGACC

GAGGTGCAGACCGGCGGCTTCAGCAAGGAGAGCATCCTGCCCAAGAGGAACAG

CGACAAGCTGATCGCCAGGAAGAAGGACTGGGACCCCAAGAAGTACGGCGGCTT

CGACAGCCCCACCGTGGCCTACAGCGTGCTGGTGGTGGCCAAGGTGGAGAAGGG

CAAGAGCAAGAAGCTGAAGAGCGTGAAGGAGCTGCTGGGCATCACCATCATGG

AGAGGAGCAGCTTCGAGAAGAACCCCATCGACTTCCTGGAGGCCAAGGGCTACA

AGGAGGTGAAGAAGGACCTGATCATCAAGCTGCCCAAGTACAGCCTGTTCGAGC

TGGAGAACGGCAGGAAGAGGATGCTGGCCAGCGCCGGCGAGCTGCAGAAGGGC

AACGAGCTGGCCCTGCCCAGCAAGTACGTGAACTTCCTGTACCTGGCCAGCCACT

ACGAGAAGCTGAAGGGCAGCCCCGAGGACAACGAGCAGAAGCAGCTGTTCGTG

GAGCAGCACAAGCACTACCTGGACGAGATCATCGAGCAGATCAGCGAGTTCAGC

AAGAGGGTGATCCTGGCCGACGCCAACCTGGACAAGGTGCTGAGCGCCTACAAC

AAGCACAGGGACAAGCCCATCAGGGAGCAGGCCGAGAACATCATCCACCTGTTC

ACCCTGACCAACCTGGGCGCCCCCGCCGCCTTCAAGTACTTCGACACCACCATCG

ACAGGAAGAGGTACACCAGCACCAAGGAGGTGCTGGACGCCACCCTGATCCACC

AGAGCATCACCGGCCTGTACGAGACCAGGATCGACCTGAGCCAGCTGGGCGGCG

ACGGCCCCGGCGAGAACCTGTACTTCCAGGGCGCCGGCGACTACAAGGACGACG

ACGACAAGGGCTGAUAA
```

A. Expression

The nucleic acid molecules may be used to express large quantities of fusion proteins. If the nucleic acid molecules are derived from a non-human, non-transgenic animal, the nucleic acid molecules may be used for antibody humanization.

1. Vectors

In some aspects, contemplated are expression vectors comprising a nucleic acid molecule encoding a polypeptide of the desired sequence or a portion thereof (e.g., a fragment containing one or more CDRs or one or more variable region domains). In addition to control sequences that govern transcription and translation, vectors and expression vectors may contain nucleic acid sequences that serve other functions as well.

To express the fusion proteins, DNAs encoding partial or full-length light and heavy chains may be inserted into expression vectors such that the gene area is operatively linked to transcriptional and translational control sequences. Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Such sequences and methods of using the same are well known in the art.

2. Expression Systems

Numerous expression systems exist that comprise at least a part or all of the expression vectors discussed above. Prokaryote- and/or eukaryote-based systems can be employed for use with an embodiment to produce nucleic acid sequences, or their cognate polypeptides, proteins and peptides. Commercially and widely available systems include in but are not limited to bacterial, mammalian, yeast, and insect cell systems. Different host cells have characteristic and specific mechanisms for the post-translational processing and modification of proteins. Appropriate cell lines or host systems can be chosen to ensure the correct modification and processing of the foreign protein expressed. Those skilled in the art are able to express a vector to produce a nucleic acid sequence or its cognate polypeptide, protein, or peptide using an appropriate expression system.

3. Methods of Gene Transfer

Suitable methods for nucleic acid delivery to effect expression of compositions are anticipated to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Other methods include viral transduction, such as gene transfer by lentiviral or retroviral transduction.

4. Host Cells

In another aspect, contemplated are the use of host cells into which a recombinant expression vector has been introduced. Fusion proteins can be expressed in a variety of cell types. An expression construct encoding a fusion protein can be transfected into cells according to a variety of methods known in the art. Vector DNA can be introduced into prokaryotic or eukaryotic cells via conventional transformation or transfection techniques. Some vectors may employ control sequences that allow it to be replicated and/or expressed in both prokaryotic and eukaryotic cells.

For stable transfection of mammalian cells, it is known, depending upon the expression vector and transfection technique used, only a small fraction of cells may integrate the foreign DNA into their genome. In order to identify and select these integrants, a selectable marker (e.g., for resistance to antibiotics) is generally introduced into the host cells along with the gene of interest. Cells stably transfected with the introduced nucleic acid can be identified by drug selection (e.g., cells that have incorporated the selectable marker gene will survive, while the other cells die), among other methods known in the arts.

VII. Additional Therapeutic Interventions

Certain embodiments concern administering a fusion protein ribonucleotide complex or disrupted immune cell described herein and an additional therapeutic intervention. The additional therapeutic intervention may be any intervention useful for treating a disease in an individual including, but not limited to, a small molecule, a biologic, an immunotherapy, surgery, radiation, or a combination thereof.

The additional therapy may be radiation therapy, surgery, chemotherapy, gene therapy, DNA therapy, viral therapy, RNA therapy, immunotherapy, bone marrow transplantation, nanotherapy, monoclonal antibody therapy, protein therapy, or a combination of the foregoing. The additional therapy may be in the form of adjuvant or neoadjuvant therapy. The additional therapy may be one or more agents that target the gene of interest (such as SRC-3) or its gene product (a protein of interest), such as antibodies of any kind, small molecule inhibitors, nucleic acids, proteins, or a combination thereof.

In some embodiments, the additional therapy is the administration of small molecule inhibitor of the protein of interest or anti-metastatic agent. In some embodiments, the additional therapy is the administration of small molecule inhibitor of SRC-3 or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

A CRISPR/Cas9/targeting antibodygene targeting sgRNA fusion protein/ribonucleotide complex may be administered before, during, after, or in various combinations relative to an additional cancer therapy. A CRISPR/Cas9/targeting antibody/SRC-3 gene targeting sgRNA fusion protein/ribonucleotide complex may be administered before, during, after, or in various combinations relative to an additional cancer therapy. The administrations may be in intervals ranging from concurrently to minutes to hours to days to weeks. In embodiments where the CRISPR/Cas9/targeting antibody/gene targeting sgRNA fusion protein/ribonucleotide complex therapy is provided to a patient separately from an additional therapeutic agent, one would generally ensure that a significant period of time did not expire between the time of each delivery, such that the two compounds would still be able to exert an advantageously combined effect on the patient.

Administration of any compound or therapy of the present embodiments to an individual will follow general protocols for the administration of such compounds, taking into account the toxicity, if any, of the agents. Therefore, in some embodiments there is a step of monitoring toxicity that is attributable to combination therapy.

A. Checkpoint Inhibitors and Combination Treatment

Embodiments of the disclosure may include administration of immune checkpoint inhibitors, which are further described below. In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4. Another immune checkpoint that can be targeted in the methods provided herein is the cytotoxic T-lymphocyte-associated protein 4 (CTLA-4), also known as CD152. In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

1. PD-1, PDL1, and PDL2 Inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PDL1 on epithelial cells and tumor cells. PDL2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PDL1 activity.

Alternative names for “PD-1” include CD279 and SLEB2. Alternative names for “PDL1” include B7-H1, B7-4, CD274, and B7-H. Alternative names for “PDL2” include B7-DC, Btdc, and CD273. In some embodiments, PD-1, PDL1, and PDL2 are human PD-1, PDL1 and PDL2.

In some embodiments, the PD-1 inhibitor is a molecule that inhibits the binding of PD-1 to its ligand binding partners. In a specific aspect, the PD-1 ligand binding partners are PDL1 and/or PDL2. In another embodiment, a PDL1 inhibitor is a molecule that inhibits the binding of PDL1 to its binding partners. In a specific aspect, PDL1 binding partners are PD-1 and/or B7-1. In another embodiment, the PDL2 inhibitor is a molecule that inhibits the binding of PDL2 to its binding partners. In a specific aspect, a PDL2 binding partner is PD-1. The inhibitor may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some embodiments, the PD-1 inhibitor is an anti-PD-1 antibody (e.g., a human antibody, a humanized antibody, or a chimeric antibody). In some embodiments, the anti-PD-1 antibody is selected from the group consisting of nivolumab, pembrolizumab, and pidilizumab. In some embodiments, the PD-1 inhibitor is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PDL1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 inhibitors include MEDI0680, also known as AMP-514, and REGN2810.

In some embodiments, the immune checkpoint inhibitor is a PDL1 inhibitor such as Durvalumab, also known as MEDI4736, atezolizumab, also known as MPDL3280A, avelumab, also known as MSB00010118C, MDX-1105, BMS-936559, or combinations thereof. In certain aspects, the immune checkpoint inhibitor is a PDL2 inhibitor such as rHIgM12B7.

In some embodiments, the inhibitor comprises the heavy and light chain CDRs or VRs of nivolumab, pembrolizumab, or pidilizumab. Accordingly, in one embodiment, the inhibitor comprises the CDR1, CDR2, and CDR3 domains of the VH region of nivolumab, pembrolizumab, or pidilizumab, and the CDR1, CDR2 and CDR3 domains of the VL region of nivolumab, pembrolizumab, or pidilizumab. In another embodiment, the antibody competes for binding with and/or binds to the same epitope on PD-1, PDL1, or PDL2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

2. CTLA-4, B7-1, and B7-2

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an “off” switch when bound to B7-1 (CD80) or B7-2 (CD86) on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4, B7-1, and/or B7-2 activity. In some embodiments, the inhibitor blocks the CTLA-4 and B7-1 interaction. In some embodiments, the inhibitor blocks the CTLA-4 and B7-2 interaction.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as a checkpoint inhibitor in the methods and compositions of the disclosure is ipilimumab (also known as 10D1, MDX-010, MDX-101, and Yervoy®) or antigen binding fragments and variants thereof (see, e.g., WO0 1/14424).

In some embodiments, the inhibitor comprises the heavy and light chain CDRs or VRs of tremelimumab or ipilimumab. Accordingly, in one embodiment, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another embodiment, the antibody competes for binding with and/or binds to the same epitope on PD-1, B7-1, or B7-2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

B. Immunotherapy

In some embodiments, the methods comprise administration of a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumour-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immumotherapies are known in the art, and some are described below.

The skilled artisan will understand that additional immunotherapies to those encompassed herein may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells.

Antibody-drug conjugates have emerged as a breakthrough approach to the development of cancer therapeutics. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. In some embodiments, ADCs are used as an additional therapeutic intervention. The approval of two ADC drugs, ADCETRIS® (brentuximab vedotin) in 2011 and KADCYLA® (trastuzumab emtansine or T-DM1) in 2013 by FDA validated the approach, merely as examples.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

1. Inhibition of Co-Stimulatory Molecules

In some embodiments, the immunotherapy comprises an inhibitor of a co-stimulatory molecule. In some embodiments, the inhibitor comprises an inhibitor of B7-1 (CD80), B7-2 (CD86), CD28, ICOS, OX40 (TNFRSF4), 4-1BB (CD137; TNFRSF9), CD40L (CD40LG), GITR (TNFRSF18), and combinations thereof. Inhibitors include inhibitory antibodies, polypeptides, compounds, and nucleic acids.

C. CAR-T Cell Therapy

Chimeric antigen receptors (CARs, also known as chimeric immunoreceptors, chimeric T cell receptors or artificial T cell receptors) are engineered receptors that combine a new specificity with an immune cell to target cancer cells. Typically, these receptors graft the specificity of a monoclonal antibody onto a T cell. The receptors are called chimeric because they are fused of parts from different sources. CAR-T cell therapy refers to a treatment that uses such transformed cells for cancer therapy.

The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. Once the T cell has been engineered to become a CAR-T cell, it acts as a "living drug". CAR-T cells create a link between an extracellular ligand recognition domain to an intracellular signalling molecule which in turn activates T cells. The extracellular ligand recognition domain is usually a single-chain variable fragment (scFv). An important aspect of the safety of CAR-T cell therapy is how to ensure that only cancerous tumor cells are targeted, and not normal cells. The specificity of CAR-T cells is determined by the choice of molecule that is targeted.

Exemplary CAR-T therapies include Tisagenlecleucel (Kymriah) and Axicabtagene ciloleucel (Yescarta). In some embodiments, the CAR-T therapy targets CD19.

D. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFNα and IFNβ), type II (IFNγ) and type III (IFNλ).

Interleukins have an array of immune system effects. IL-2 is an exemplary interleukin cytokine therapy.

E. Adoptive T-Cell Therapy

Adoptive T cell therapy is a form of passive immunization by the transfusion of T-cells (adoptive cell transfer). They are found in blood and tissue and usually activate when they find foreign pathogens. Specifically they activate when the T-cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumour death.

Multiple ways of producing and obtaining tumour targeted T-cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

It is contemplated that a cancer treatment may exclude any of the cancer treatments described herein. Furthermore, embodiments of the disclosure include patients that have been previously treated for a therapy described herein, are currently being treated for a therapy described herein, or have not been treated for a therapy described herein. In some embodiments, the patient is one that has been determined to be resistant to a therapy described herein. In some embodiments, the patient is one that has been determined to be sensitive to a therapy described herein.

F. Chemotherapies

In some embodiments, the additional therapy comprises a chemotherapy. A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Suitable classes of chemotherapeutic agents include alkylating agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan, improsulfan, and piposulfan), nitrosoureas (e.g., carmustine, lomustine, chlorozoticin, streptozocin) and triazines (e.g., dicarbazine), antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), natural products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and miscellaneous agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine e oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda;

ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above. In some embodiments, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m2 to about 20 mg/m2 for 5 days every three weeks for a total of three courses being contemplated in certain embodiments. In some embodiments, the amount of cisplatin delivered to the cell and/or subject in conjunction with the construct comprising an Egr-1 promoter operably linked to a polynucleotide encoding the therapeutic polypeptide is less than the amount that would be delivered when using cisplatin alone.

Other suitable chemotherapeutic agents include antimicrotubule agents, e.g., Paclitaxel ("Taxol") and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain embodiments, appropriate intravenous doses for an adult include about 60 mg/m2 to about 75 mg/m2 at about 21-day intervals or about 25 mg/m2 to about 30 mg/m2 on each of 2 or 3 successive days repeated at about 3 week to about 4 week intervals or about 20 mg/m2 once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the disclosure. A nitrogen mustard may include, but is not limited to, mechlorethamine (HN2), cyclophosphamide and/or ifosfamide, melphalan (L-sarcolysin), and chlorambucil. Cyclophosphamide (CYTOXAN®) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

G. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

H. Radiotherapy

In some embodiments, the additional therapy or prior therapy comprises radiation, such as ionizing radiation. As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some embodiments, the amount of ionizing radiation is greater than 20 Gy and is administered in one dose. In some embodiments, the amount of ionizing radiation is 18 Gy and is administered in three doses. In some embodiments, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some embodiments, the ionizing radiation is administered in at least, at most, or exactly 1, 2, 3, 4, 5, 6, 7, 8, 9, or 10 does (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some embodiments, the amount of IR may be presented as a total dose of IR, which is then administered in fractionated doses. For example, in some embodiments, the total dose is 50 Gy administered in 10 fractionated doses of 5 Gy each. In some embodiments, the total dose is 50-90 Gy, administered in 20-60 fractionated doses of 2-3 Gy each. In some embodiments, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some embodiments, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein. In some embodiments, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some embodiments, at least, at most, or exactly 1, 2, 3, 4, 5, 6, 7, 8, 9, 10, 11, or 12 (or any derivable range therein) fractionated doses are administered per day. In some embodiments, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

VIII. Treatment of Diseases

In some embodiments, the present disclosure provides methods for cancer treatment or treatment of inborn errors of metabolism, hematopoietic diseases, inflammatory diseases, and/or genetic diseases affecting liver function that employ immunotherapy. In certain embodiments, methods and compositions described herein are used for treating, delaying progression of, delaying onset of, or reducing the risk of getting a disease, including a cancer, in an individual. In some embodiments, the methods and compositions are administered to the individual a therapeutically effective amount the fusion protein ribonucleotide complex, such as the CRISPR/Cas9/targeting antibody/gene targeting small guide RNA (sgRNA) fusion protein/ribonucleotide complex.

In certain embodiments, the inborn errors of metabolism include, but are not limited to, glycogen storage disease, G6PD deficiency, phenylketonuria, maple syrup urine disease, glutaric acidemia type 1, carbamoyl phosphate synthetase I deficiency, alkaptonuria, combined malonic and methylmalonic aciduria, 2-hydroxyglutaric acidurias, medium-chain acyl-coenzyme A dehydrogenase deficiency, acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann-Pick disease.

In certain embodiments, the hematopietic diseases include, but are not limited to, bone marrow failure disorders such as Fanconi anemia, thrombocytopenia with absent radius syndrome, Diamond-Blackfan anemia, Schwachman-Diamond Syndrome, and cartilage-hair hypoplasia; disorders of hemoglobin such as sickle cell disease, and thalassemia; disorders of neutrophils and lymphocytes such as chronic granulomatous disease, and X-linked agammaglobulinemia; and disorders of the monocyte-macrophage system such as Gaucher disease.

In certain embodiments, the inflammatory diseases include, but are not limited to, an allergy, asthma, an autoimmune disease, coeliac disease, glomerulonephritis, hepatitis, inflammatory bowel disease, preperfusion injury, transplant rejection, ankylosing spondylitis (AS), gout, myositis, rheumatoid arthritis, scleroderma, Sjogren's Syndrome, systemic lupus Erythematosus, pelvic inflammatory disease, or vasculitis In certain embodiments, the genetic diseases affecting liver function include, but are not limited to, hemochromatosis and alpha-1 anti-trypsin deficiency.

The present methods may be applied for the treatment of solid cancers or hematologic cancers. The cancer may be primary, metastatic, refractory to therapy, and so forth. The cancer may be of any type and of any stage. The individual may be at risk for cancer, including over the general population, and the individual at risk for cancer may be so because of a personal or family history, because the individual is a tobacco user, is obese, consumes excessive alcohol, has some types of viral infections, such as human papillomavirus (HPV), has exposure to one or more carcinogens, or has had excessive exposure to radiation, including ultraviolet radiation from the sun. An amount may be considered excessive when it is greater than the average individual of a population.

Tumors for which the disclosed treatment methods are useful include any malignant cell type, such as those found in a solid tumor or a hematological tumor. In some embodiments, solid tumors can include, but are not limited to, a tumor of an organ selected from the group consisting of breast, ovary, pancreas, colon, cecum, stomach, brain, head, neck, kidney, larynx, sarcoma, lung, bladder, melanoma, prostate, gastric tissue, and endometrium. In some embodiments, hematological tumors include tumors of the bone marrow, T or B cell malignancies, leukemias, lymphomas, blastomas, myelomas, and the like. Particular examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer encompassed herein may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, mjmalignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

In certain embodiments of the present disclosure, immune cells are delivered to an individual in need thereof, such as an individual that has cancer or is suspected of having cancer. In some embodiments, the administered cells enhance the individual's immune system to attack the respective cancer. In some cases, the individual is provided with one or more doses of the immune cells and/or any CRISPR/Cas9/targeting antibody/gene targeting sgRNA fusion protein/ribonucleotide complex described herein. In cases where the individual is provided with two or more doses, the duration between the administrations is sufficient to allow time for propagation of targeted Tregs in the individual, and in specific embodiments the duration between doses is 1, 2, 3, 4, 5, 6, 7, or more days. In some cases, the duration between administrations is 1-24 hours, 1-7 days, 1-4 weeks, 1-12 months, or more, or any range derivable there between.

In some embodiments, the subject can be administered nonmyeloablative lymphodepleting chemotherapy prior to the immune cell therapy and/or complex therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, including when the cancer is melanoma, which can be metastatic. In certain embodiments, the route of administering cyclophosphamide and fludarabine is intravenously. Likewise, any suitable dose of cyclophosphamide and/or fludarabine can be administered. In particular aspects, around 60 mg/kg of cyclophosphamide is administered for two days after which around 25 mg/m2 fludarabine is administered for five days.

In certain embodiments, a growth factor or cytokine that promotes the growth and activation of immune cells is administered to the subject either concomitantly with the CRISPR/Cas9/targeting antibody/gene targeting sgRNA fusion protein/ribonucleotide complex. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of the CRISPR/Cas9/targeting antibody/gene targeting sgRNA fusion protein/ribonucleotide complex can be administered by a number of routes, including parenteral administration, for example, intravenous, intraperitoneal, intramuscular, intrasternal, or intraarticular injection, intranasal, intraarterial, or by infusion.

In some embodiments, the therapeutically effective amount of the CRISPR/Cas9/targeting antibody/gene targeting sgRNA fusion protein/ribonucleotide complex is an amount that achieves a desired effect in a subject being treated. For instance, this can be the amount of CRISPR/Cas9/targeting antibody/gene targeting sgRNA fusion protein/ribonucleotide complex necessary to inhibit growth, or to cause regression of cancer, or improve at least one symptom of cancer.

In some embodiments, the therapeutically effective amount of the CRISPR/Cas9/targeting antibody/SRC-3 gene targeting sgRNA fusion protein/ribonucleotide complex is an amount that achieves a desired effect in a subject being treated. For instance, this can be the amount of CRISPR/Cas9/targeting antibody/SRC-3 gene targeting sgRNA fusion protein/ribonucleotide complex necessary to inhibit growth, or to cause regression of cancer, or improve at least one symptom of cancer.

The immune cell population can be administered in treatment regimens consistent with the disease. For example, a single or multiple doses over can be administered over one to several days to ameliorate a disease state or periodic doses over an extended time to inhibit disease progression and prevent disease recurrence. The precise dose to be employed in the formulation will also depend on the route of administration and the seriousness of the disease or disorder, and should be decided according to the judgment of the practitioner and the individual's circumstances. The therapeutically effective amount of immune cells will be dependent on the subject being treated, the severity and type of the affliction, and the manner of administration. In some embodiments, doses that could be used to target Tregs residing within human subjects that range from at least $3.8\times10^4$, at least $3.8\times10^5$, at least $3.8\times10^6$, at least $3.8\times10^7$, at least $3.8\times10^8$, at least $3.8\times10^9$, or at least $3.8\times10^{10}$ immune cells/$m^2$. In a certain embodiment, the dose used in the treatment of human subjects ranges from about $3.8\times10^9$ to about $3.8\times10^{10}$ immune cells/$m^2$. In additional embodiments, a therapeutically effective amount of CRISPR/Cas9/targeting antibody/gene targeting sgRNA fusion protein/ribonucleotide complex that can target $5\times10^6$ $T_{reg}$ cells per kg body weight to about $7.5\times10^8$ cells per kg body weight, such as about $2\times10^7$ cells to about $5\times10^8$ cells per kg body weight, or about $5\times10^7$ cells to about $2\times10^8$ cells per kg body weight. The exact amount of CRISPR/Cas9/targeting antibody/gene targeting sgRNA fusion protein/ribonucleotide complex is readily determined by one of skill in the art based on the age, weight, sex, and physiological condition of the subject. Effective doses can be extrapolated from dose-response curves derived from in vitro or animal model test systems.

The CRISPR/Cas9/targeting antibody/gene targeting sgRNA fusion protein/ribonucleotide complex may be administered in combination with one or more other therapeutic agents for the treatment of the cancer. The CRISPR/Cas9/targeting antibody/SRC-3 gene targeting sgRNA fusion protein/ribonucleotide complex may be administered in combination with one or more other therapeutic agents for the treatment of the cancer. Combination therapies can include, but are not limited to, one or more anti-tumor agents or a vaccine. In specific cases, chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered in addition to the immune cells. Such additional pharmaceutical agents can be administered before, during, or after administration of the immune cells, depending on the desired effect. This administration of the cells and the one or more additional anti-cancer agents can be by the same route or by different routes, and either at the same site or at a different site.

IX. Administration of Therapeutic Compositions

The therapy provided herein may comprise administration of a combination of therapeutic agents, such as a first fusion protein ribonucleotide complex therapy and a second therapy, including any additional therapeutic intervention described herein. The therapies may be administered in any suitable manner known in the art. For example, the first therapy and second therapy may be administered sequentially (at different times) or concurrently (at the same time). In some embodiments, the first and second therapies are administered in a separate composition. In some embodiments, the first and second therapies are in the same composition.

In some embodiments, the first therapy and the second therapy are administered substantially simultaneously. In some embodiments, the first therapy and the second therapy are administered sequentially. In some embodiments, the first therapy and the second therapy, and a third therapy are administered sequentially. In some embodiments, the first therapy and the second therapy. In some embodiments, the first therapy and the second therapy.

Embodiments of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some embodiments, the cancer therapy is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

In some embodiments, a single dose of the fusion protein ribonucleotide complex protein therapy is administered. In some embodiments, multiple doses of the fusion protein ribonucleotide complex are administered. In some embodiments, the fusion protein ribonucleotide complex protein is administered at a dose of between 1 mg/kg and 5000 mg/kg. In some embodiments, the fusion protein ribonucleotide complex protein is administered at a dose of at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 mg/kg.

In some embodiments, a single dose of the additional therapeutic intervention is administered. In some embodiments, multiple doses of the additional therapeutic intervention are administered. In some embodiments, the additional therapeutic intervention is administered at a dose of between 1 mg/kg and 100 mg/kg. In some embodiments, the additional therapeutic intervention is administered at a dose of at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 μg/kg, mg/kg, μg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 μM to 150 μM. In another embodiment, the effective dose provides a blood level of about 4 μM to 100 μM; or about 1 μM to 100 μM; or about 1 μM to 50 μM; or about 1 μM to 40 μM; or about 1 μM to 30 μM; or about 1 μM to 20 μM; or about 1 μM to 10 μM; or about 10 μM to 150 μM; or about 10 μM to 100 μM; or about 10 μM to 50 μM; or about 25 μM to 150 μM; or about 25 μM to 100 μM; or about 25 μM to 50 μM; or about 50 μM to 150 μM; or about 50 μM to 100 μM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of μg/kg or mg/kg of body weight can be converted and expressed in comparable concentration units of μg/ml or mM (blood levels), such as 4 μM to 100 μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, or 12 week intervals, including all ranges there between.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, anti-bacterial and anti-fungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the intravenous, intramuscular, subcutaneous, or intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including, for example, aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various anti-bacterial and anti-fungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to, oral, or intravenous administration. Alternatively, administration may be by orthotopic, intradermal, subcutaneous, intramuscular, intraperitoneal, or intranasal administration. Such compositions would normally be administered as pharmaceutically acceptable compositions that include physiologically acceptable carriers, buffers or other excipients.

Upon formulation, solutions will be administered in a manner compatible with the dosage formulation and in such amount as is therapeutically or prophylactically effective. The formulations are easily administered in a variety of dosage forms, such as the type of injectable solutions described above.

A. Pharmaceutical Compositions

Provided herein, in some embodiments, are pharmaceutical compositions and formulations comprising fusion protein ribonucleotide complexes, including a CRISPR/Cas9/CD25 targeting antibody/gene targeting sgRNA fusion protein/ribonucleotide complex, and a pharmaceutically acceptable carrier. Provided herein, in some embodiments, are pharmaceutical compositions and formulations comprising a CRISPR/Cas9/targeting antibody/SRC-3 gene targeting sgRNA fusion protein/ribonucleotide complex, and a pharmaceutically acceptable carrier. Pharmaceutical compositions and formulations as described herein can be prepared by mixing the active ingredient (such as the CRISPR/Cas9/CD25 targeting antibody/gene targeting sgRNA fusion protein/ribonucleotide complex) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

In some embodiments, the carrier is non-toxic, biocompatible and is selected so as not to detrimentally affect the biological activity of the agent in the carrier. The agents in some aspects of the disclosure may be formulated into preparations for local delivery (i.e. to a specific location of the body) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable or solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antgifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol may be between about 0.01 ml and 0.5 mL, for example.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

X. Articles of Manufacture or Kits

An article of manufacture or a kit is provided comprising any fusion protein/ribonucleotide complex disclosed herein. The kit may comprise one or more reagents to produce the targeted disruption (including, e.g., nucleic acids and proteins that facilitate knockout or knockdown of the gene specifically), one or more agents that target a gene product of interest, buffers, salts, directions for use, or a combination thereof.

The article of manufacture or kit can further comprise a package insert comprising instructions for using the fusion protein/ribonucleotide complex to treat or delay progression of cancer in an individual. Suitable containers include, for example, bottles, vials, bags and syringes. The container may be formed from a variety of materials such as glass, plastic (such as polyvinyl chloride or polyolefin), or metal alloy (such as stainless steel or a nickel-molybdenum alloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A fusion protein ribonucleotide complex comprising a fusion protein and at least one single guide RNA (sgRNA) targeting an SRC-3 gene, wherein the fusion protein comprises:

at least one antibody or antibody fragment; and at least one RNA-guided DNA endonuclease, and wherein the at least one sgRNA targeting the SRC-3 gene has a nucleotide sequence comprising at least 15 consecutive nucleotides of SEQ ID NO: 24.

2. The complex of claim 1, wherein the RNA-guided DNA endonuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or a functional derivative thereof.

3. The complex of claim 1, wherein the RNA-guided DNA endonuclease is Cas9.

4. The complex of claim 1, wherein the fusion protein further comprises a linker domain between the antibody, or antibody fragment, and the RNA-guided DNA endonuclease.

5. The complex of claim 1, wherein the fusion protein further comprises one or more purification tags.

6. The complex of claim 5, wherein the purification tag is selected from the group consisting of His tag, FLAG-tag, HA, calmodulin binding peptide, cellulose binding domain, chitin biding domain, albumin-binding protein, AU1 epitope, AU5 epitope, biotin-carboxy carrier protein, galactose-binding protein, glutathione S-transferase, Halotag, streptavidin-binding peptide, and any combination thereof.

7. The complex of claim 1, wherein the fusion protein further comprises one or more proteases.

8. The complex of claim 7, wherein the protease is selected from the group consisting of Tobacco Etch Virus (TEV) protease, Enterokinase, PreScission protease, Enteropeptidase, thrombin, 3C protease, Factor Xa, and any combination thereof.

9. The complex of claim 1, wherein the antibody fragment is an scFv.

10. The complex of claim 9, wherein the antibody or antibody fragment targets a cell surface protein.

11. The complex of claim 9, wherein the antibody or antibody fragment targets a cancer antigen.

12. The complex of claim 1, wherein the antibody or antibody fragment targets CD19, CD4, HER2, PD-1, CTLA-4, TGFBR, or EGFR.

13. A therapeutic composition comprising the complex of claim 1.

14. The therapeutic composition of claim 13, further comprising a pharmaceutically acceptable carrier.

15. The complex of claim 1, wherein the fusion protein further comprises a cell penetrating peptide.

16. The complex of claim 15, wherein the cell penetrating peptide comprises KLALKLALKALKAALK (SEQ ID NO:2).

17. The complex of claim 15, wherein the cell penetrating peptide is encoded by AAGCTGGCCCTGAAGCTGGCCCTGAAGGCCCTGAAGGCCGCCCTGAAG (SEQ ID NO:13).

18. The complex of claim 1, wherein the at least one sgRNA targeting the SRC-3 gene has a nucleotide sequence comprising SEQ ID NO: 24.

* * * * *